(12) United States Patent
Rueckl et al.

(10) Patent No.: US 11,141,376 B2
(45) Date of Patent: Oct. 12, 2021

(54) CIRCULATION OF COMPONENTS DURING MICROFLUIDIZATION AND/OR HOMOGENIZATION OF EMULSIONS

(71) Applicant: Novartis AG, Basel (CH)

(72) Inventors: Harald Rueckl, Alsfeld (DE); Hanno Scheffczik, Marburg (DE); Barbara Santry, Meath (IE)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/571,813

(22) Filed: Sep. 16, 2019

(65) Prior Publication Data

US 2020/0268661 A1 Aug. 27, 2020

Related U.S. Application Data

(63) Continuation of application No. 15/632,562, filed on Jun. 26, 2017, now Pat. No. 10,463,615, which is a continuation of application No. 14/478,864, filed on Sep. 5, 2014, now abandoned, which is a continuation of application No. 13/513,564, filed as application
(Continued)

(51) Int. Cl.
| | |
|---|---|
| *A61K 9/107* | (2006.01) |
| *A61K 39/39* | (2006.01) |
| *B01F 13/10* | (2006.01) |
| *B01F 3/08* | (2006.01) |
| *B01F 5/06* | (2006.01) |
| *A61K 39/00* | (2006.01) |
| *B01F 7/00* | (2006.01) |

(52) U.S. Cl.
CPC ............ *A61K 9/1075* (2013.01); *A61K 9/107* (2013.01); *A61K 39/39* (2013.01); *B01F 3/0807* (2013.01); *B01F 5/0661* (2013.01); *B01F 7/00766* (2013.01); *B01F 13/1016* (2013.01); *A61K 2039/55566* (2013.01)

(58) Field of Classification Search
None
See application file for complete search history.

(56) References Cited

U.S. PATENT DOCUMENTS

| | | |
|---|---|---|
| 4,533,254 A | 8/1985 | Cook et al. |
| 5,487,965 A | 1/1996 | Odell |

(Continued)

FOREIGN PATENT DOCUMENTS

| | | |
|---|---|---|
| CN | 1767854 | 5/2006 |
| CN | 1956729 | 5/2007 |

(Continued)

OTHER PUBLICATIONS

SPX (Multiple Pass Homogenization by continuous recycling, Feb. 2009). (Year: 2009).*

(Continued)

*Primary Examiner* — Melissa S Mercier
(74) *Attorney, Agent, or Firm* — Duane Morris LLP; Thomas J. Kowalski; Deborah L. Lu

(57) ABSTRACT

An improved method for the manufacture of an oil-in-water emulsion involves circulation of emulsion components between a first container and a second container via a homogenizer and/or via a microfluidization device. Usefully, all of the emulsion components from the first container are emptied before being returned.

24 Claims, 4 Drawing Sheets

Related U.S. Application Data

No. PCT/IB2010/003394 on Dec. 3, 2010, now Pat. No. 8,895,629.

(60) Provisional application No. 61/283,518, filed on Dec. 3, 2009.

(56) References Cited

U.S. PATENT DOCUMENTS

| | | | |
|---|---|---|---|
| 5,510,118 | A | 4/1996 | Bosch et al. |
| 5,565,203 | A | 10/1996 | Gluck et al. |
| 6,168,718 | B1 | 1/2001 | Sutter et al. |
| 6,331,314 | B1 | 12/2001 | Klinksiek et al. |
| 6,364,919 | B1 | 4/2002 | Lee et al. |
| 6,645,463 | B1 | 11/2003 | Counsell et al. |
| 7,122,191 | B2 | 10/2006 | Dominowski et al. |
| 7,238,349 | B1 | 7/2007 | Houdt et al. |
| 7,959,931 | B2 * | 6/2011 | Colegate ............ A61P 31/12 424/209.1 |
| 8,182,792 | B2 | 5/2012 | Muhrer et al. |
| 8,187,554 | B2 | 5/2012 | Panagiotou et al. |
| 8,506,966 | B2 | 8/2013 | Podda et al. |
| 8,678,184 | B2 | 3/2014 | Kraus |
| 8,771,727 | B2 | 7/2014 | Dominowski et al. |
| 8,778,275 | B2 | 7/2014 | Rueckl et al. |
| 8,871,816 | B2 | 10/2014 | Rueckl |
| 8,895,629 | B2 * | 11/2014 | Rueckl ............... B01F 7/00766 514/763 |
| 9,463,240 | B2 | 10/2016 | Rueckl |
| RE46,441 | E * | 6/2017 | Rueckl ............... B01F 5/0661 |
| 9,700,616 | B2 | 7/2017 | Rueckl et al. |
| 9,750,690 | B2 | 9/2017 | Rueckl et al. |
| RE46,906 | E * | 6/2018 | Rueckl ............... A61K 39/39 |
| 10,463,615 | B2 * | 11/2019 | Rueckl ............... B01F 5/0661 |
| 2004/0029977 | A1 | 2/2004 | Kawa et al. |
| 2004/0258701 | A1 | 12/2004 | Dominowski et al. |
| 2005/0220814 | A1 * | 10/2005 | Dominowski ......... A61P 31/12 424/204.1 |
| 2006/0144973 | A1 | 7/2006 | Greenwood et al. |
| 2006/0148776 | A1 | 7/2006 | Ulm |
| 2006/0251684 | A1 | 11/2006 | Annis et al. |
| 2007/0172426 | A1 | 7/2007 | Lee et al. |
| 2007/0248632 | A1 | 10/2007 | Goget et al. |
| 2008/0026981 | A1 | 1/2008 | Muhrer et al. |
| 2008/0069832 | A1 | 3/2008 | Chomez et al. |
| 2009/0258043 | A1 | 10/2009 | Eskuchen et al. |
| 2009/0263422 | A1 | 10/2009 | Hanon et al. |
| 2010/0173854 | A1 | 7/2010 | Dominowski et al. |
| 2011/0162982 | A1 | 7/2011 | Kraus et al. |
| 2011/0165193 | A1 | 7/2011 | Rueckl et al. |
| 2012/0315308 | A1 | 12/2012 | Travers |
| 2013/0129786 | A1 | 5/2013 | Kraus et al. |
| 2015/0017206 | A1 | 1/2015 | Rueckl et al. |
| 2016/0113870 | A1 | 4/2016 | Rueckl et al. |

FOREIGN PATENT DOCUMENTS

| | | |
|---|---|---|
| CN | 1972670 | 5/2007 |
| DE | 195 42 499 | 5/1997 |
| DE | 100 59 430 | 6/2002 |
| EP | 1 020 760 | 7/2000 |
| EP | 0 770 422 | 9/2002 |
| EP | 1 574 210 | 9/2005 |
| GB | 1009671.7 | 11/1965 |
| TW | 2006/11880 | 4/2006 |
| WO | 1990/14837 | 12/1990 |
| WO | 1994/05298 | 3/1994 |
| WO | 2000/050006 | 8/2000 |
| WO | 2002/043672 | 6/2002 |
| WO | 2004/082625 | 9/2004 |
| WO | 2004/087204 | 10/2004 |
| WO | 2005/027872 | 3/2005 |
| WO | 2005/089718 | 9/2005 |
| WO | 2006/008504 | 1/2006 |
| WO | 2006/050837 | 5/2006 |
| WO | 2006/100110 | 9/2006 |
| WO | 2006/100111 | 9/2006 |
| WO | 2007/098186 | 8/2007 |
| WO | 2008/051186 | 5/2008 |
| WO | 2008/068631 | 6/2008 |
| WO | 2009/123595 | 10/2009 |
| WO | 2009/132171 | 10/2009 |
| WO | 2009/155401 | 12/2009 |
| WO | 2011/067669 | 6/2011 |
| WO | 2011/067672 | 6/2011 |
| WO | 2011/067673 | 6/2011 |
| WO | 2011/154442 | 12/2011 |

OTHER PUBLICATIONS

SPX (Multiple Pass Homogenization by continuous recycling, Feb. 2009).
Merck Millipore. "Sterile Millipak-60 Filter Unit 0.22 µm ¼ in. HB/HB w/bell-Capsule Filters" Information Sheet, Jun. 16, 2014.
Merck Millipore. "Sterilizing-grade Durapore 0.1 µm and 0.22 µm Hydrophilic Filters" Data Sheet, 2012.
Microfluidics International Annual Report, 76 pages (2007).
Millipore Corporation. Durapore CBR 0.2 µm Bioburden Reduction Filters, Information Sheet, 2006.
Millipore & Fisher Scientific. Durapore 0.1 µm and 0.22 µm Hydrophilic Filters, Data Sheet, 2009.
Notice of Opposition to a European Patent—Opposition against the grant of European Patent Application No. 2506832, Patent Application No, 2010807661.3, Mention of date of grant: Feb. 26, 2014, Statement of Opposition filed by GlaxoSmithKline Biologicals, 20 pages, dated Nov. 25, 2014.
Notice of Opposition to a European Patent—Opposition against the grant of European Patent Application No. 2506833, Patent Application No. 2010812802, Date of Grant: Apr. 16, 2014, Opposition filed by Merial Limited, 30 pages, dated Jan. 14, 2015.
Notice to File Missing Parts in U.S. Appl. No. 61/283,517, 2 pages, dated Jan. 12, 2010.
Notice to File Missing Parts of Provisional Application dated Jan. 11, 2010, which issued in U.S. Appl. No. 61/283,548.
Opposition Brief dated Jan. 27, 2016, which was filed during the opposition of Japanese Application No. 2012-541594.
Pall Corporation. New Hybrid Filters Accelerate Processing of High-Yield Biotech Drugs (2006) Accessed Nov. 20, 2014 http://news.pall.com/article display.cfm?article id=4324.
Patil, et al., Formulation of a self-emulsifying system for oral delivery of simvastatin: In vitro and in vivo evaluation, Acta Pharm. (2007) 57:111-122.
Pope, Turbulent Flows, p. 186, Cambridge New York: Cambridge University Press (2000).
Reif, Microfiltration Membranes: Characteristics and Manufacturing, Adv. Biochem Engin/Biotechnol (2006) 98:73-103.
Response to Appeal No. T2385/15 in European Patent No. 2380558 filed Nov. 18, 2016.
Response to Notice of Opposition filed Aug. 28, 2015, submitted in European Application No. 2 506 833.
Response to Notice to File Missing Parts in U.S. Appl. No. 61/283,517, 6 pages, filed Mar. 3, 2010.
Response to Summons to Oral Proceedings in European Patent No. 2506833 filed Sep. 5, 2016.
Sanders et al., Protein Delivery: Physical Systems, p. 180, New York: Plenum Press (1997).
Sartorius Stedim Biotech, Sartobran P 0.2 µm Sterilizing Grade Filter Cartidges, Information Sheet, Version 4 2009.
Schultze et al., Safety of MF59TM Adjuvant, Vaccine (2008) 26:3209-3222.
Seubert et al., The Adjuvants Aluminum Hydroxide and MF59 Induce Monocyte and Granulocyte Chemoattractants and Enhance Monocyte Differentiation toward Dendritic Cells, The Journal of immunology, 180(8):5402-5412 (2008).
Streeter et al., Fluid Mechanics, McGraw-Hill, Sixth Edition, 23 pages (1975).
Summons to Attend Oral Proceedings of European Patent 2601933, Sep. 21, 2017.

(56) References Cited

OTHER PUBLICATIONS

Translation of TW Application No. 2006/11880 filed Oct. 14, 2004.
U.S. Non-Final Rejection dated Jul. 28, 2016, which issued during prosecution of U.S. Appl. No. 15/076,776.
U.S. Non-Final Rejection dated Sep. 8, 2015, which issued during prosecution of U.S. Appl. No. 14/657,165.
U.S. Appl. No. 61/283,517, 46 pages, filed Dec. 3, 2009.
Updated Filing Receipt mailed Mar. 15, 2010 which issued in U.S. Appl. No. 61/283,517.
Updated Filing Receipt mailed Mar. 15, 2010, issued in U.S. Appl. No. 61/283,548.
White. Fluid Mechanics, McGraw-Hill, Chapter 5, pp. 306,316,317 (2008).
Written Transcript of Public Webinar delivered by Dr. Panagiotou on Jun. 18, 2009. 13 pages.
File History of EP 2 356 983 as of Jul. 13, 2015.
File History of EP 2 506 834 as of May 7, 2015.
U.S. Non-Final Rejection and Notice of References Cited dated Aug. 16, 2016, issued in U.S. Appl. No. 14/881,410.
Submission in Opposition Proceedings made following Summons to Attend Oral Proceedings for EP Patent 2 506 833 dated Jan. 5, 2018.
Submission under Rule 116 EPC dated Jan. 5, 2018, for EP Patent 2 506 833.
Annex B to the Ramina Declaration dated Jan. 4, 2018.
Annex C2 to the Ramina Declaration dated Jan. 4, 2018, evidencing sale to Customer 2 (Goldschmidt AG).
Annex C3 to the Ramina Declaration dated Jan. 4, 2018, evidencing sale to Customer 3 (Schering Corp.
Annex C4 to the Ramina Declaration dated Jan. 4, 2018, evidencing sale to Customer 4 (G.C. Hanford Mfg.).
Declaration of Finnian O'Callaghan dated Jan. 5, 2018.
Declaration of Jocemar Ramina dated Jan. 4, 2018.
Ott, et al., Design and Evaluation of a Safe and Potent Adjuvant for Human Vaccines, Vaccine Design, The Subunit and Adjuvant Approach, pp. 277-296 (1995).
Ott, et al., The Adjuvant MF59: A 10-Year Perspective, Methods in Molecular Medicine, 42:211-228, (2000).
Pall Corporation, "Product data sheet for Polyethersulfone Membranes" 2012.
Panagiotou, Microfluidizer Processor Technology, Laboratory to Full Production, MicroTAS Konferenze (2007).
Podda, et al., MF59 Adjuvant Emulsion, Chapter 19, New Generation Vaccines, 3rd Edition, pp. 225-235 (2005).
Podda, et al, MF59-Adjuvanted Vaccines: Increased Immunogenicity with an Optimal Safety Profile, Expert Rev. Vaccines, 2(2): 197-204 (2003).
Sartorius Stedim Biotech, Bioprocess Catalogue Products and Solutions for the Biopharmaceutical Industry, Sartorius 2009.
Sartorius Stedim Biotech, Sartorius Stedim Biotech Launches Sartopore® 2 Gamma Midicaps, Bioresearch Online, Oct. 20, 2009.
Silverson, Batch Mixers—How It Works, Mar. 7, 2015, retrieved from: http://www.silverson.eo.uk/en/products/patch-mixer/how-it-works.
Silverson, Batch Mixers—Technical Information, Mar. 7, 2015, retrieved from: http://www.silverson.eo.uk/en/products/batch-mixers/technical-information.
SPX Flow Technology, APV Flex-Mix In-line Mixer—Type Dar, Mar. 2012.
SPX Flow Technology, APV Rannie and Gaulin Homogenisers, Aug. 2013.
SPX, Multiple-Pass Homogenization by Continuous Recycling, APV Technical Bulletin #71, (2009).
Statement of Grounds of Appeal filed in European Application No. 2 356 983 on Jul. 7, 2015.
U.S. Final Rejection dated Aug. 14, 2014 issued in U.S. Appl. No. 13/508,986.
U.S. Non-Final Office Action dated Jul. 29, 2016 issued in U.S. Appl. No. 14/478,818.
U.S. Non-Final Office Action dated Sep. 25, 2012 issued in U.S. Appl. No. 12/928,163.
U.S. Non-Final Rejection dated Jan. 30, 2014, issued in U.S. Appl. No. 13/508,986.
High Filtration Area Membrane Filters Available in European Market, Filtration and Separation, 40(7):12 (2003).
Annex B to Ramina Declaration—Schedule of MFIC Multi-slotted APM orders Aug. 1, 2000, Customer 1.
Annex C1 to Ramina Declaration—Microfluidics Machine Order dated Aug. 1, 2000, Customer 1.
Annex C2 to Ramina Declaration—Microfluidics Machine Order dated Jan. 19, 2001, Customer 2.
Annex C3 to Ramina Declaration—Microfluidics Machine Order dated Mar. 28, 2001, Customer 3.
Annex P.1 to Dr. Thomai Panagiotou Declaration—Summary of Experimental Results on Oil in Water Emulsions (castor oil and squalene), Detailing Impact of Microfluidizer Configuration on Particle Size Reduction, Sep. 24, 2014.
Annex P.2 to Panagiotou Declaration of Sep. 24, 2014.
Annex P.3 to Panagiotou Declaration of Sep. 24, 2014.
Araya, et al., The novel formulation design of self-emulsifying drug delivery systems (SEDDS) type O/W microemulsion II: stable gastrointestinal absorption of a poorly water soluble new compound, ER-1258 in bile-fistula rats, Drug Metab. Pharmacokinet, 2005, 20(4);257-267.
Assignment for U.S. Appl. No. 61/283,548, signed by Hanno Scheffczik on Oct. 27, 2010.
Assignment for U S. Appl. No. 61/283,548, signed by Harald Rueckl on Nov. 8, 2010.
Assignment for U.S. Appl. No. 61/283,548, signed by Novartis Vaccines on Nov. 10, 2010.
Assignment recorded in U.S. Appl. No. 61/283,517 signed Oct. 14, 2010, Reel 025206, Frame 0685 and 0686, Recorded Oct. 27, 2010, assigning to Novartis Vaccines and Diagnostics Gmbh, 2 pages.
Assignment recorded in U.S. Appl. No. 61/283,517 signed Oct. 14, 2010, Reel 025946, Frame 0435 and 0436, Recorded Mar. 14, 2011, assigning to Novartis Vaccines and Diagnostics Gmbh, 2 pages.
Assignment recorded in U.S. Appl. No. 61/283,517 signed Oct. 21, 2010, Reel 025206, Frame 0729 and 0730, Recorded Oct. 27, 2010, assigning from Novartis Vaccines and Diagnostics Gmbh to Novartis AG, 2 pages.
Auxiliary Request 1—Claim 1 as amended. (Cited in the Response to Notice of Opposition filed Aug. 28, 2015, submitted in European Application No. 2 506 833).
Auxiliary Request 2—Claim 1 as amended. (Cited in the Response to Notice of Opposition filed Aug. 28, 2015, submitted in European Application No. 2 506 833).
Auxiliary Request 3—Claim 1 as amended. (Cited in the Response to Notice of Opposition filed Aug. 28, 2015, submitted in European Application No. 2 506 833).
Auxiliary Request 4—Claim 1 as amended. (Cited in the Response to Notice of Opposition filed Aug. 28, 2015, submitted in European Application No. 2 506 833).
Auxiliary Request 5—Claim 1 as amended. (Cited in the Response to Notice of Opposition filed Aug. 28, 2015, submitted in European Application No. 2 506 833).
Baudner et al., MF59 Emulsion is an Effective Delivery System for a Synthetic TLR4 Agonist (E6020), Pharmaceutical Research, 26(6):1477-1485 (2009).
Cardona et al., Filtration Design Remove Processing Bottlenecks for High-Yield Biotech Drugs, BioPharmaInternational.com (2006), Accessed Nov. 20, 2014 hltg:/lwww.biopharminternational.com/biopharm/Downstream+Processing/Filtration-Designs-Remove-Processing-Bottlenecks/Article/detail/329352.
Cardona et al., Pleated Membrane Filters Improve Process Economics, BioPharmaInternational.com (2005) Accessed Nov. 20, 2014 http://www.biopharminternational.com/biopharm/article/articleDetail.jsp?id=146217.
Chomistek, et al., Large Scale Nanomaterial Production Using Microfluidizer High Shear Processing, Materials Research Society Symposium, 2010, vol. 1209.
Slides of Public Webinar delivered by Dr. Panagiotou on Jun. 18, 2009, 43 pages.

(56) References Cited

OTHER PUBLICATIONS

Curriculum Vitae of Harald Rucki. (Cited in the Response to Notice of Opposition filed Aug. 28, 2015, submitted in European Application No. 2 506 833).
Decision of the Opposition Division to revoke EP 2506832 dated Mar. 24, 2016.
Declaration of Dr. Thomai Panagiotou, 19 pages, Sep. 24, 2014.
Declaration of Harald Rueckl dated Sep. 24 2014.
Declaration of Jocemar Ramina dated Sep. 2, 2016.
Declaration of Professor Robert J. Fisher, 23 pages, dated Sep. 24, 2014.
Declaration of Thomai Panagiotou dated Feb. 17, 2016.
Declaration of Thomai Panagiotou dated Sep. 3, 2016.
Dupuis, et al. Immunization with the adjuvant MF59 induces macrophage trafficking and apoptosis, Eur. J. Immunol., 2001, 31:2910-2918.
FiberFlo Hollow Fiber Cartridge Filters. Product Information, 4 pages. (2003).
Global Patents, Response to Submissions dated Dec. 15, 2015.
Information Disclosure Statement filed in U.S. Appl. No. 12/928,165, filed Nov. 6, 2012, 4 pages.
Japanese Office Action in corresponding JP 2012-541594, 4 pages, dated Dec. 1, 2014 (English Translation).
Jornitz et al., Sterile Filtration—A Review of the Past and Present Technologies, PDA Journal of Pharmaceutical Science and Technology, 56(4):192-195 (2002).
Khulbe et al., Synthetic Membranes for Membrane Process, Chapter 2, Synthetic Membrane for Membrane Process, p. 5-18 (2008) Springer Berlin Heidelberg Print ISBN 978-3-540-73993-7.
Kong et al., Plasmid DNA Processing for Gene Therapy and Vaccination: Studies on the Membrane Sterilisation C: Filtration Step, Journal of Membrane Science, 280:824-831 (2006).
Krackeler Scientific Inc. Schleicher and Schuell Membrane Filters, Jul. 27, 2015.
Kundu and Cohen, Dynamic Similarity, p. 279, Fluid Mechanics, Burlington: Elsevier (2007).
Lachman, et al., The Theory and Practice of Industrial Pharmacy. pp. 152-154, Nov. 1986.
List of Invitees to Public Webinar delivered by Dr. Panagiotou on Jun. 18, 2009, 1 page.
List of Invitees to Public Webinar delivered by Dr. Panagiotou on Jun. 18, 2009, 24 pages.
Merck Millipore. Durapore Membrane Filters—Filter Discs and Membranes Jul. 17, 2015.
Merck Millipore. Millex-GV Syringe Filter Unit, 0.22 μm, PVDF, 33 mm, gamma sterilized, Information Sheet, Jun. 16, 2014.
Merck Millipore. Millipak Disposable Filter Units—Dialysis and Filtration, Information Sheet, Jul. 27, 2015.
Merck Millipore. "Sterile Millipak-200 Filter Unit 0.22 μm 9/16 in. HB/HB-Sterile Filtration" Information Sheet, Jun. 16, 2014.
Chinese First Office Action dated May 31, 2017, issued in Chinese Application No. 201510552611.1.
Letter from Bradford Besse, VP Microfluidics International Corporation in relation to D29b and D31a, Mar. 2, 2018.
Microfluidics Proposal, including Standard Terms & Conditions, for sale to G.C. Hanford Mfg. (D31a), Jun. 21, 2000.
Microfluidics Proposal, including Standard Terms & Conditions, for sale to Goldschmidt AG (D29b), Aug. 16, 2000.
Microfluidics Standard Terms & Conditions as revised May 2006.
Written Submission of Merial Limited dated Mar. 3, 2018, submitted during opposition proceedings of European Patent No. 2506833.
Allison. Squalene and Squalane Emulsions as Adjuvants, Methods, 19:87-93 (1999).
AVESTIN Webpage: http://www.avestin.com/English/fx_html (2013).
AVESTIN Webpage: http://www.avestin.com/English/staticvalvepage.html (2013).
Bakan, et al., Physicochemical Characterization of a Synthetic Lipid Emulsion for Hepatocyte-Selective Delivery of Lipophilic Compounds: Application to Polyiodinated Triglycerides as Contrast Agents for Computed Tomography, Journal of Pharmaceutical Sciences, 85(9):908-914, (1996).
Case details for Trade Mark EU 001531797—(Excerpt from UKIPO Trademark Register showing Gaulin is a registered trademark for high pressure homogenizers) Mar. 7, 2015.
Charles Ross & Son Company: High-capacity rotor/stator mixers, Mixing Technology Insight #76, retrieved ram: http://www.mixers.com/insightPDF.asp?pdf=mti_76.pdf, 2014.
Claims filed in European Application No. 2 356 983 on Jul. 7, 2015.
Claims of European Patent 2 506 834 dated Mar. 2015.
Decision of Opposition dated Feb. 25, 2015 issued in European Patent 2 356 983.
Declaration of Harald Rueckl submitted in European Patent 2 356 983 dated Feb. 27, 2015.
Dick, Novel Fat-Free Drug Delivery Systems for the Anesthetic 2,6-Diisopropylphenol, Ph.D. Thesis submitted to the Department of Chemistry of Philipps University Marburg (2007), English translation attached.
Dixit, et al., Biopharmaceutical Industry: The Importance of Prefiltration, Filtration and Separation, pp. 24-26, Jul.-Aug. 2007.
Dixit, Membranes and Filtration: Membrane Filtration in the BioPharm Industry, Filtration and Separation, pp. 18-21, Oct. 2008.
Driesens, Effects of Glass on h-dependent stability of typhoid vaccine, Journal of Clinical Microbiology, 2(2):85-88 (1975).
Dunleavy, Polyethesulfone Membranes Facilitate Sterile Filtration of Biological Materials, BioScience Technol. 44:S46 (2003).
European Search Report and Opinion dated Jun. 1, 2011 which issued during prosecution of European Application No. 10252044.
Forschungskreis der Ernahrungsindustrie e.V. (FEI), Energy-Saving and Gentle Homogenization of Milk and its Effects on the Texture of Milk Products, pp. 1-4 (2007) in German and with certified English translation, Retrieved from: http://www.wzw.tum.de/blm/imvt/ncu/pdf/homo_lang.pdf.
Gaulin Corporation. "Gaulin Homogenizers".
Harald Ru Eckl Curriculcum Vitae, 2015.
International Preliminary Report on Patentability dated Jul. 27, 2012, issued in International Patent Application No. PCT/IB2010/003273.
International Preliminary Report on Patentability dated Jul. 27, 2012, issued in International Patent Application No. PCT/IB2010/003394.
International Search Report dated Jun. 1, 2011 issued in International Patent Application No. PCT/IB2010/003273.
International Search Report dated Mar. 13, 2012 issued in International Patent Application No. PCT/IB2010/003394.
Jafari, et al., Re-coalescence of emulsion droplets during high-energy emulsification, Food Hydrocolloids 22:1191-1202 (2008).
Jornitz, et al., Modern Sterile Filtration—The Economics, Pharmaceutical Technology Europe, pp. 29-32, Jun. 2003.
Kirkland Products. "Kirkland Handheld Emulsifier" Mar. 7, 2015, retrieved from: http://www.kirklandproducts.com/emulsifier.
Konan, et al., Preparation and Characterization of Sterile and Freeze-Dried Sub-200nm Nanoparticles, International Journal of Pharmaceuticals, 233(1-2):239-252, (2002).
Lidgate, et al, Sterile Filtration of a Parenteral Emulsion, Pharmaceutical Research, 9(7):860-863 (1992).
Lidgate, Development of an Emulsion-based Muramyl Dipeptide Adjuvant Formulation for Vaccines, Vaccine Design—The Subunit and Adjuvant Approach, Chapter 12, pp. 313-324, 1995.
Little, et al., The shorter Oxford English Dictionary, 3rd edition. 1073.1 751, Oxford University Press, 1973.
Little, et al., The shorter Oxford English Dictionary, 3rd edition. 1073.2 1612, Oxford University Press, 1973.
Microfluidics, Corixa Study Shows Microfluidizer Processor Results Superior to those of Leading Homogenizer (2010).
Microfluidics, M-610 Series. M-610 Production Scale Microfluidizer Processor (2010).
Microfluidics, M-110S Microfluidizer Materials Data Sheet, available online (1998).
Microfluidics, Microfluidizer Processor User Guide, Innovation Through Microfluidizer Processor Technology, Microfluidics (Apr. 24, 1998).

(56) References Cited

OTHER PUBLICATIONS

Microfluidics, Microfluidizer Processor User guide, Innovation Through Microfluidizer Processor Technology, Microfluidics (Sep. 17, 2008).
Microfluidics, M-700 Series Microfluidizer Materials Processor, Microfluidizer Processor for Continuous High Shear Fluid Processing in Industrial Environments (2010).
Microfluidics, Model M-110Y Microfluidizer Processor, User's Manual (2008).
Microfluidics, Model M-11 OY Microfluidizer Processor. High Pressure Laboratory Microfluidizer Processor for High-Shear Fluid Processing (2010).
Microfluidics, Model M-210 EH Microfluidizer Processor User's Manual (2003).
Minutes of Oral Proceedings held Apr. 16, 2015, 2014 for EP Patent 2 506 834.
Minutes of Oral Proceedings held Dec. 15, 2014 for EP Patent 2 356 983.
Notice of Opposition to European Patent 2380558 by Intervet International BV dated Jun. 11, 2013.
Notice of Opposition to European Patent 2380558 by Merial Limited dated Jun. 11, 2013.
Notice of Opposition to European Patent 2380558 by Microfluidics Corporation dated Jun. 11, 2013.
Notice of Opposition to European Patent No. 2343052 dated Mar. 12, 2014, pages 1-6.
Notice of Opposition to European Patent No. 2356983 dated Nov. 19, 2013.
O'Hagan, et al., The Adjuvant MF59: A 10-year Perspective, Methods in Molecular Medicine, Vaccine Adjuvants, Preparation Methods and Research Protocols, 42:211-228 (2000).
Opposition against grant of European Patent EP 2356983 dated Nov. 19, 2013.
Opposition against grant of European Patent No. 2343052 dated Mar. 12, 2014.
U.S. Appl. No. 14/881,410, Application as filed Oct. 13, 2015.
U.S. Appl. No. 14/881,575, Application as filed Oct. 13. 2015.

\* cited by examiner

Flow Rate: 1.2 gpm @ 30 kpsi
(4.54 lpm @ 2068 bar)

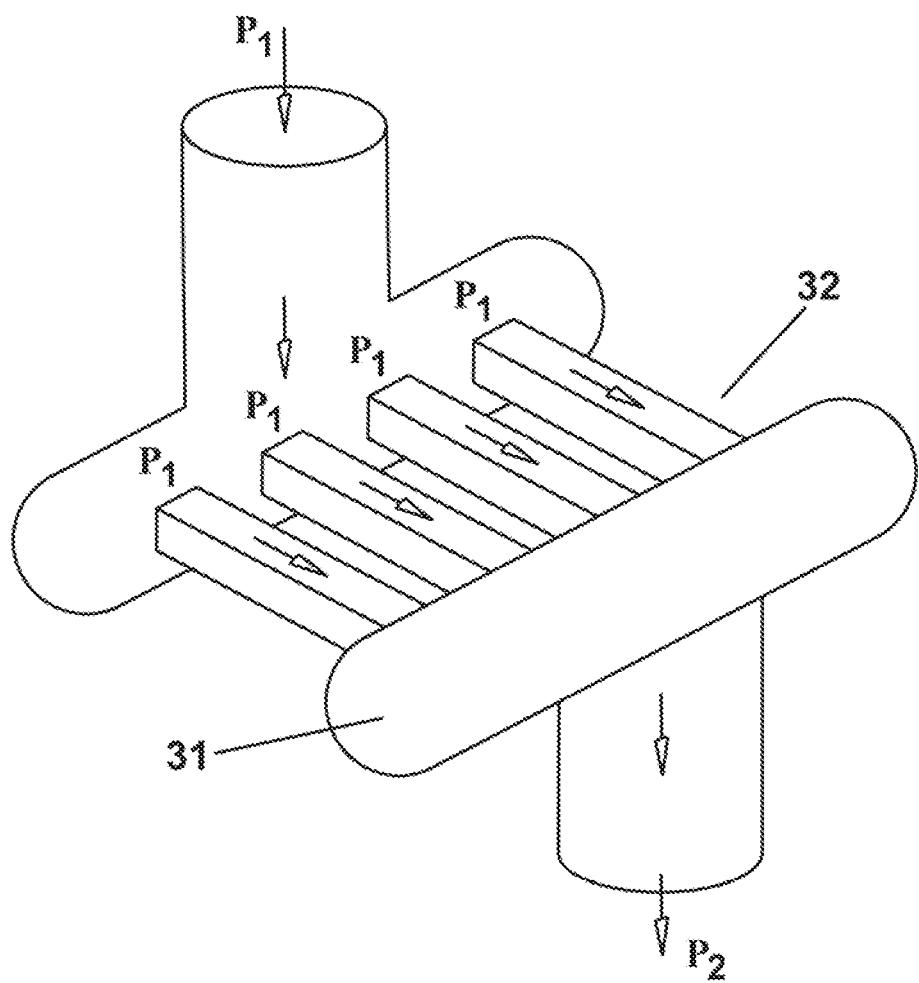

US 11,141,376 B2

CIRCULATION OF COMPONENTS DURING MICROFLUIDIZATION AND/OR HOMOGENIZATION OF EMULSIONS

This application is a continuation of U.S. patent application Ser. No. 15/632,562 filed Jun. 26, 2017, allowed, which is a continuation of U.S. patent application Ser. No. 14/478,864 filed on Sep. 5, 2014, abandoned, which is a continuation of U.S. patent application Ser. No. 13/513,564 filed on Feb. 20, 2013, now U.S. Pat. No. 8,895,629, which subsequently reissued as RE46,441 on Jun. 20, 2017; U.S. patent Ser. No. 13/513,561 is a 35 U.S.C. § 371 National Stage of International Application No. PCT/IB2010/003394 entitled "CIRCULATION OF COMPONENTS DURING HOMOGENIZATION EMULSIONS" filed on Dec. 3, 2010, which claims the benefit of and priority to U.S. Provisional Application No. 61/283,518 filed Dec. 3, 2009, the complete contents of which are incorporated herein by reference for all purposes.

TECHNICAL FIELD

This invention is in the field of manufacturing oil-in-water emulsion adjuvants for vaccines by microfluidization.

BACKGROUND ART

The vaccine adjuvant known as 'MF59' [1-3] is a submicron oil-in-water emulsion of squalene, polysorbate 80 (also known as Tween 80), and sorbitan trioleate (also known as Span 85). It may also include citrate ions e.g. 10 mM sodium citrate buffer. The composition of the emulsion by volume can be about 5% squalene, about 0.5% Tween 80 and about 0.5% Span 85. The adjuvant and its production are described in more detail in Chapter 10 of reference 4, chapter 12 of reference 5 and chapter 19 of reference 6.

As described in reference 7, MF59 is manufactured on a commercial scale by dispersing Span 85 in the squalene phase and Tween 80 in the aqueous phase, followed by high-speed mixing to form a coarse emulsion. This coarse emulsion is then passed repeatedly through a microfluidizer to produce an emulsion having a uniform oil droplet size. As described in reference 6, the microfluidized emulsion is then filtered through a 0.22 µm membrane in order to remove any large oil droplets, and the mean droplet size of the resulting emulsion remains unchanged for at least 3 years at 4° C. The squalene content of the final emulsion can be measured as described in reference 8.

Oil-in-water emulsions contain oil droplets. The larger oil droplets contained in these emulsions may act as nucleation sites for aggregation, leading to emulsion degradation during storage.

It is an object of the invention to provide further and improved methods for the production of microfluidized oil-in-water emulsions (such as MF59), in particular methods that are suitable for use on a commercial scale and which provide improved homogenization and microfluidization to provide emulsions with fewer large particles.

BRIEF DESCRIPTION OF THE DRAWINGS

FIG. 4 shows a Z-type channel interaction chamber.

FIG. 5 shows a type I circulation, whereas In FIG. 6 the homogenizer has two input arrows and two output arrows but in reality the homogenizer has a single input channel and a single output channel.

DISCLOSURE OF THE INVENTION

Figure 1:
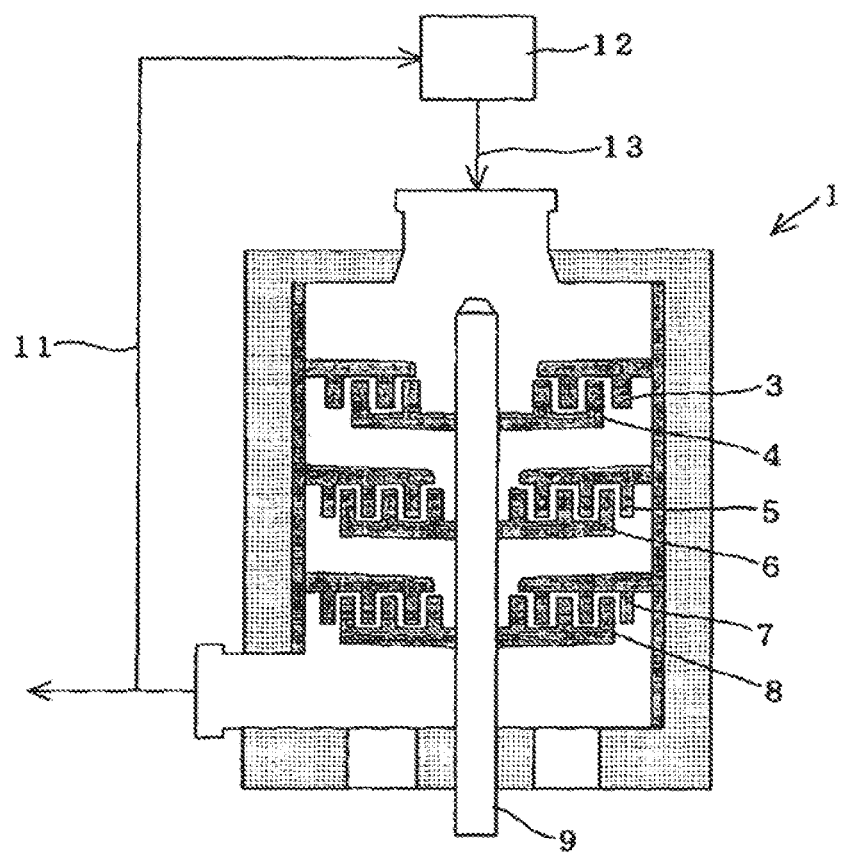
FIG. 1 shows a specific example of a homogenizer that can be used to form a first emulsion.
Figure 2:
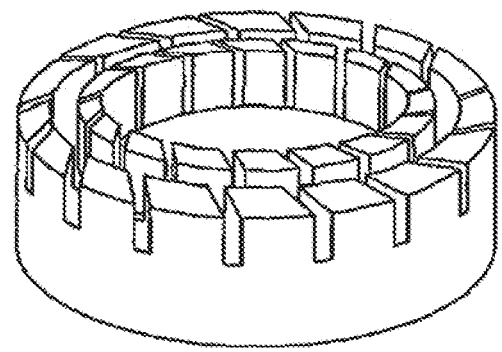
FIG. 2 shows detail of a rotor and stator that can be used in such a homogenizer.

The invention provides a method for the manufacture of an oil-in-water emulsion comprising squalene, the method comprising the step of (i) formation of a first emulsion having a first average oil droplet size using a homogenizer, wherein the first emulsion is formed by circulating the first emulsion components through a homogenizer a plurality of times.

The invention also provides a method for the manufacture of an oil-in-water emulsion comprising squalene, the method comprising the step of: (b) microfluidization of a first emulsion having a first average oil droplet size to form a second emulsion having a second average oil droplet size which is less than the first average oil droplet size, wherein the second emulsion is formed by circulating the second emulsion components by transferring the second emulsion components from a first emulsion container, through a first microfluidization device to a second emulsion container, and then through a second microfluidization device, wherein the first and second microfluidization devices are the same.

Optionally, the method of the present invention comprises an earlier step of (a) formation of a first emulsion having a first average oil droplet size.

Optionally, the method of the present invention comprises the step of (c) filtration of the second emulsion.

As described in more detail below, the first emulsion may have an average oil droplet size of 5000 nm or less e.g. an average size between 300 nm and 800 nm. The number of oil droplets in the first emulsion with a size >1.2 µm may be $5 \times 10^{11}$/ml or less, as described below. Oil droplets with a size >1.2 µm are disadvantageous as they can cause instability of the emulsion due to agglomeration and coalescence of droplets [14].

After formation, the first emulsion may then be subjected to at least one pass of microfluidization to form the second emulsion having a reduced average oil droplet size. As described below, the average oil droplet size of the second emulsion is 500 nm or less. The number of oil droplets in the second emulsion having a size >1.2 µm may be $5 \times 10^{10}$/ml or less, as described below. To achieve these characteristics it may be necessary to pass the emulsion components through the microfluidization device a plurality of times, e.g. 2, 3, 4, 5, 6, 7 times.

The second emulsion may then be filtered, e.g. through a hydrophilic polyethersulfone membrane, to give an oil-in-water emulsion that may be suitable for use as a vaccine adjuvant. The average oil droplet size of the oil-in-water emulsion produced after filtration may be 220 nm or less, e.g. between 135-175 nm, between 145-165 nm, or about 155 nm. The number of oil droplets having a size >1.2 µm present in the oil-in-water emulsion produced after filtration may be $5 \times 10^8$/ml or less, e.g. $5 \times 10^7$/ml or less, $5 \times 10^6$/ml or less, $2 \times 10^6$/ml or less or $5 \times 10^5$/ml or less.

The final oil-in-water emulsion formed after filtration may have at least $10^2$ times fewer oil droplets having a size >1.2 µm in comparison to the first emulsion, and ideally at least $10^3$ times fewer (e.g. $10^4$ times fewer).

In some embodiments, more than one cycle of steps (i) and (ii) is used prior to step (iii). Similarly, multiple repeats of individual steps (i) and (ii) may be used.

In general, the method is performed between 20-60° C., and ideally at 40±5° C. Although the first and second emulsion components may be relatively stable even at higher temperatures, thermal breakdown of some components can still occur and so lower temperatures are preferred.

Emulsion Components

The average oil droplet size (i.e. the number average diameter of the emulsion's oil droplets) may be measured using a dynamic light scattering technique, as described in reference 13. An example of a dynamic light scattering measurement machine is the Nicomp 380 Submicron Particle Size Analyzer (from Particle Sizing Systems).

The number of particles having a size >1.2 μm may be measured using a particle counter such as the Accusizer™ 770 (from Particle Sizing Systems).

Methods of the invention are used for the manufacture of oil-in-water emulsions. These emulsions include three core ingredients: an oil; an aqueous component; and a surfactant.

Because the emulsions are intended for pharmaceutical use then the oil will typically be biodegradable (metabolisable) and biocompatible.

The oil used may comprise squalene, a shark liver oil which is a branched, unsaturated terpenoid ($C_{30}H_{50}$; $[(CH_3)_2C\ [=CHCH_2CH_2C(CH_3)]_2=CHCH_2-]_2$; 2,6,10,15,19,23-hexamethyl-2,6,10,14,18,22-tetracosahexaene; CAS RN 7683-64-9). Squalene is particularly preferred for use in the present invention.

The oil of the present invention may comprise a mixture (or combination) of oils e.g. comprising squalene and at least one further oil.

Rather than (or on addition to) using squalene an emulsion can comprise oil(s) including those from, for example, an animal (such as fish) or a vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ε or ξ tocopherols can be used, but α-tocopherols are preferred. D-α-tocopherol and DL-α-tocopherol can both be used. A preferred α-tocopherol is DL-α-tocopherol. The tocopherol can take several forms e.g. different salts and/or isomers. Salts include organic salts, such as succinate, acetate, nicotinate, etc. If a salt of this tocopherol is to be used, the preferred salt is the succinate. An oil combination comprising squalene and a tocopherol (e.g. DL-α-tocopherol) can be used.

The aqueous component can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. Buffers will typically be included in the 5-20 mM range.

The surfactant is preferably biodegradable (metabolisable) and biocompatible. Surfactants can be classified by their 'HLB' (hydrophile/lipophile balance), where a HLB in the range 1-10 generally means that the surfactant is more soluble in oil than in water, and a HLB in the range 10-20 are more soluble in water than in oil. Emulsions preferably comprise at least one surfactant that has a HLB of at least 10 e.g. at least 15, or preferably at least 16.

The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the SPANs), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. Tween 80, with a HLB of 15.0) and a surfactant with a HLB value in the range of 1-10 (e.g. Span 85, with a HLB of 1.8).

Formation of the First Emulsion

Before the microfluidization step, emulsion components may be mixed to form a first emulsion.

Oil droplets in the first emulsion may have an average size of 5000 nm or less e.g. 4000 nm or less, 3000 nm or less, 2000 nm or less, 1200 nm or less, 1000 nm or less, e.g. an average size between 800 and 1200 nm or between 300 nm and 800 nm.

In the first emulsion the number of oil droplets with a size >1.2 μm may be $5\times10^{11}$/ml or less, e.g. $5\times10^{10}$/ml or less or $5\times10^{9}$/ml or less.

The first emulsion may then be microfluidised to form a second emulsion having a lower average oil droplet size than the first emulsion and/or fewer oil droplets with size >1.2 µm.

The average oil droplet size of the first emulsion can be achieved by mixing the first emulsion's components in a homogenizer. For instance, as shown in FIG. 1, they can be combined in a mixing vessel (12) and then the combined components can be introduced (13) into a mechanical homogenizer, such as a rotor-stator homogenizer (1).

Homogenizers can operate in a vertical and/or horizontal manner. For convenience in a commercial setting, in-line homogenizers are preferred.

The components are introduced into a rotor-stator homogenizer and meet a rapidly rotating rotor containing slots or holes. The components are centrifugally thrown outwards in a pump like fashion and pass through the slots/holes. In some embodiments the homogenizer includes multiple combinations of rotors and stators e.g. a concentric arrangement of comb-teeth rings, as shown by features (3) & (4); (5) & (6) and (7) & (8) in FIG. 1 and by FIG. 1. The rotors in useful large-scale homogenizers may have comb-teeth rings on the edge of a horizontally oriented multi-bladed impeller (e.g feature (9) in FIG. 1) aligned in close tolerance to matching teeth in a static liner. The first emulsion forms via a combination of turbulence, cavitation and mechanical shearing occurring within the gap between rotor and stator. The components are usefully introduced in a direction parallel to the rotor's axis.

An important performance parameter in rotor-stator homogenizers is the tip speed of the rotor (peripheral velocity). This parameter is a function both of rotation speed and of rotor diameter. A tip speed of at least 10 ms$^{-1}$ is useful, and ideally quicker e.g. ≥20 ms$^{-1}$, ≥30 ms$^{-1}$, ≥40 ms$^{-1}$, etc. A tip speed of 40 ms$^{-1}$ can be readily achieved at 10,000 rpm with a small homogenizer or at lower rotation speeds (e.g. 2,000 rpm) with a larger homogenizer. Suitable high-shear homogenizers are commercially available.

For commercial-scale manufacture the homogenizer should ideally have a flow rate of at least 300 L/hr e.g. ≥400 L/hr, ≥500 L/hr, ≥600 L/hr, ≥700 L/hr, ≥800 L/hr, ≥900 L/hr, ≥1000 L/hr, ≥2000 L/hr, ≥5000 L/hr, or even ≥10000 L/hr. Suitable high-capacity homogenizers are commercially available.

A preferred homogenizer provides a shear rate of between $3 \times 10^5$ and $1 \times 10^6$ s$^{-1}$, e.g. between $3 \times 10^5$ and $7 \times 10^5$ s$^{-1}$, between $4 \times 10^5$ and $6 \times 10^5$ s$^{-1}$, e.g. about $5 \times 10^5$ s$^{-1}$.

Although rotor-stator homogenizers generate relatively little heat during operation, the homogenizer may be cooled during use. Ideally, the temperature of the first emulsion is maintained below 60° C. during homogenization, e.g. below 45° C.

In some embodiments the first emulsion components may be homogenized multiple times (e.g. 2, 3, 4, 5, 6, 7, 8, 9, 10, 20, 30, 40, 50 or more times). To avoid the need for a long string of containers and homogenizers the emulsion components can instead be circulated (e.g. as shown by feature (11) in FIG. 1). In particular, the first emulsion may be formed by circulating the first emulsion components through a homogenizer a plurality of times (e.g. 2, 3, 4, 5, 6, 7, 8, 9, 10, 20, 30, 40, 50, 100 etc times). However, too many cycles may be undesirable as it can produce re-coalescence as described in reference 14. Thus the size of oil droplets may be monitored if homogenizer circulation is used to check that a desired droplet size is reached and/or that re-coalescence is not occurring.

Circulation through the homogenizer is advantageous because it can reduce the average size of the oil droplets in the first emulsion. Circulation is also advantageous because it can reduce the number of oil droplets having a size >1.2 µm in the first emulsion. These reductions in average droplet size and number of droplets >1.2 µm in the first emulsion can provide advantages in downstream process(es). In particular, circulation of the first emulsion components through the homogenizer can lead to an improved microfluidization process which may then result in a reduced number of oil droplets having a size >1.2 µm in the second emulsion, i.e. after microfluidization. This improvement in the second emulsion parameters can provide improved filtration performance. Improved filtration performance may lead to less content losses during filtration, e.g. losses of squalene, Tween 80 and Span 85 when the oil-in-water emulsion is MF59.

Figure 5:
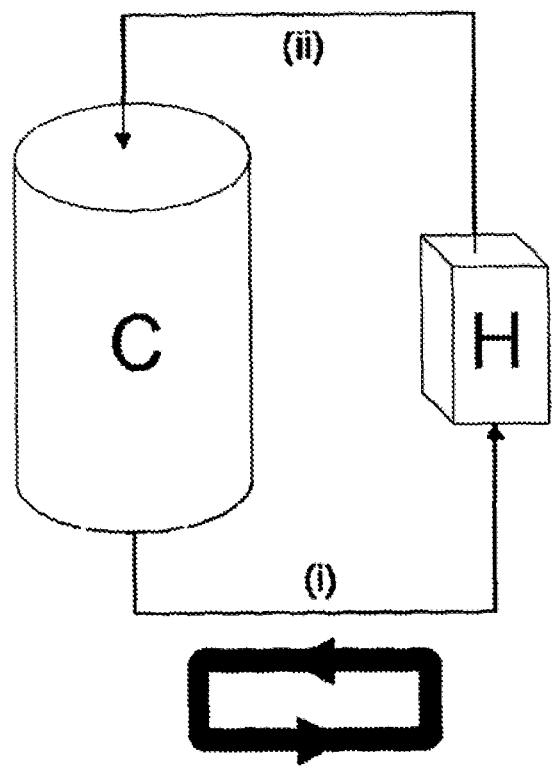
Figure 6:
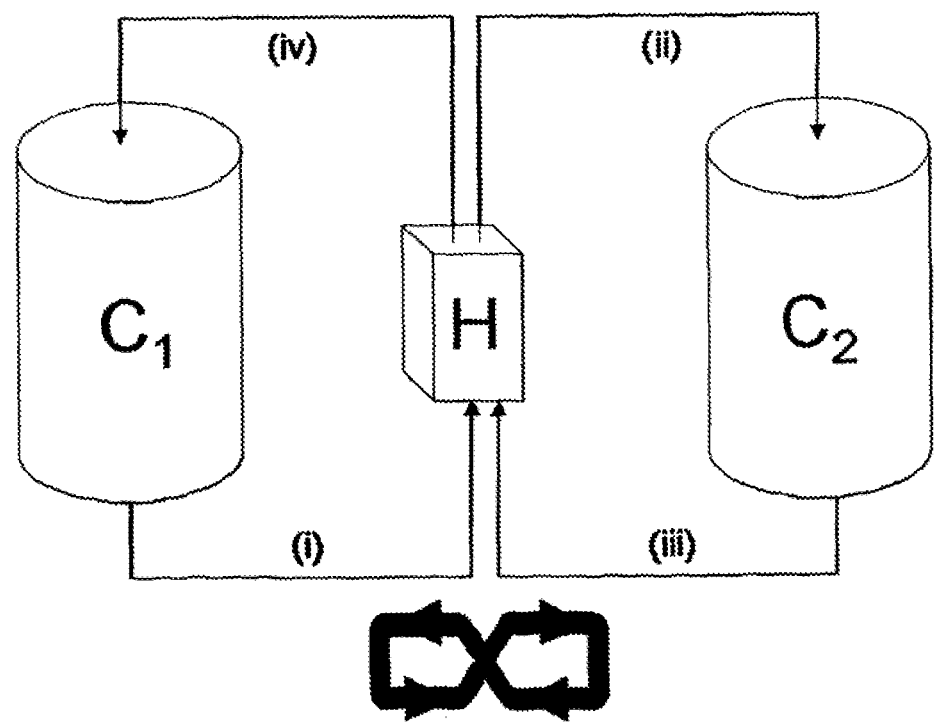
FIG. 6 shows a type II circulation. Containers are labeled as "C" whereas a homogenizer is labeled as "H". Direction and order of fluid movements are shown.

Two particular types of circulation are referred to herein as "type I" and "type II". Type I circulation is illustrated in FIG. 5, whereas type II circulation is illustrated in FIG. 6.

The circulation of the first emulsion components may comprise a type I circulation of transferring the first emulsion components between a first premix container and a homogenizer. The first premix container may be from 50 to 500 L in size, e.g. 100 to 400 L, 100 to 300 L, 200 to 300 L, 250 L or 280 L. The first premix container may be manufactured from stainless steel. The type I circulation may be continued for 10 to 60 minutes, e.g. 10 to 40 minutes or 20 minutes.

The circulation of the first emulsion components may comprise a type II circulation of transferring the first emulsion components from a first premix container, through a first homogenizer to a second premix container (optionally having the same properties as the first premix container), and then through a second homogenizer. The second homogenizer will usually be the same as the first homogenizer, but in some arrangements the first and second homogenizers are different. Following the pass of the first emulsion components through the second homogenizer, the first emulsion components may be transferred back to the first premix container, for example if the type II circulation process is to be repeated. Thus the emulsion components may travel in a figure of eight route between the first and second premix containers via a single homogenizer (see FIG. 6). Type II circulation may be carried out a single time or a plurality of times, e.g. 2, 3, 4, 5 etc times.

Type II circulation is advantageous, compared to type I circulation, because it can help to ensure that all of the components of the first emulsion pass through the homogenizer. Emptying of the first premix container means that the complete emulsion contents have passed through the homogenizer, into the second premix container. Similarly, the contents of the second premix container can be emptied, again ensuring that they all pass through the homogenizer. Thus the type II arrangement can conveniently ensure that all of the emulsion components are homogenized at least twice, which can reduce both the average size of the oil droplets and the number of oil droplets having a size >1.2 µm in the first emulsion. An ideal type II circulation thus involves emptying the first premix container and passing substantially all of its contents through the homogenizer into the second premix container, followed by emptying the second premix container and re-passing substantially all of its contents through the homogenizer back into the first (empty) premix container. Thus all particles pass through the homogenizer at least twice, which is difficult to achieve with type I circulation.

In some embodiments a combination of type I and type II circulations is used, and this combination can provide a first emulsion with good characteristics. In particular, this combination can greatly reduce of the number of oil droplets having a size >1.2 µm in the first emulsion. This combination can comprise any order of type I and II circulation, e.g., type I followed by type II, type II followed by type I, type I followed by type II followed by type I again etc. In one embodiment, the combination comprises 20 minutes of type I circulation followed by a single type II circulation, i.e. transferring the circulated first emulsion components from a first premix container, through a first homogenizer to a second premix container, and then through a second homogenizer once.

The first and second premix containers may be held under an inert gas, e.g. nitrogen, e.g. at up to 0.5 bar. This can prevent the emulsion components from oxidizing, which is particularly advantageous if one of the emulsion components is squalene. This can provide an increase in the stability of the emulsion.

As mentioned above, the initial input for the homogenizer may be a non-homogenized mixture of the first emulsion components. This mixture may be prepared by mixing the individual first emulsion components individually but, in some embodiments, multiple components can be combined prior to this mixing. For instance, if the emulsion includes a surfactant with a HLB below 10 then this surfactant may be combined with an oil prior to mixing. Similarly, if the emulsion includes a surfactant with a HLB above 10 then this surfactant may be combined with an aqueous component prior to mixing. Buffer salts may be combined with an aqueous component prior to mixing, or may be added separately.

Methods of the invention may be used at large scale. Thus a method may involve preparing a first emulsion whose volume is greater than 1 liter e.g. ≥5 liters, ≥10 liters, ≥20 liters, ≥50 liters, ≥100 liters, ≥250 liters, etc.

After its formation, the first emulsion may be microfluidized, or may be stored to await microfluidization.

In some embodiments, in particular those where multiple cycles of steps (i) and (ii) are used, the input for the homogenizer will be the output of a microfluidizer, such that the first emulsion is microfluidized and then again subjected to homogenization.

Microfluidization

After its formation the first emulsion is microfluidized in order to reduce its average oil droplet size and/or to reduce the number of oil droplets having a size of >1.2 µm.

Microfluidization instruments reduce average oil droplet size by propelling streams of input components through geometrically fixed channels at high pressure and high velocity. The pressure at the entrance to the interaction chamber (also called the "first pressure") may be substantially constant (i.e. ±15%; e.g. ±10%, ±5%, ±2%) for at least 85% of the time during which components are fed into the microfluidizer, e.g. at least 87%, at least 90%, at least 95%, at least 99% or 100% of the time during which the emulsion is fed into the microfluidizer.

Figure 3A:
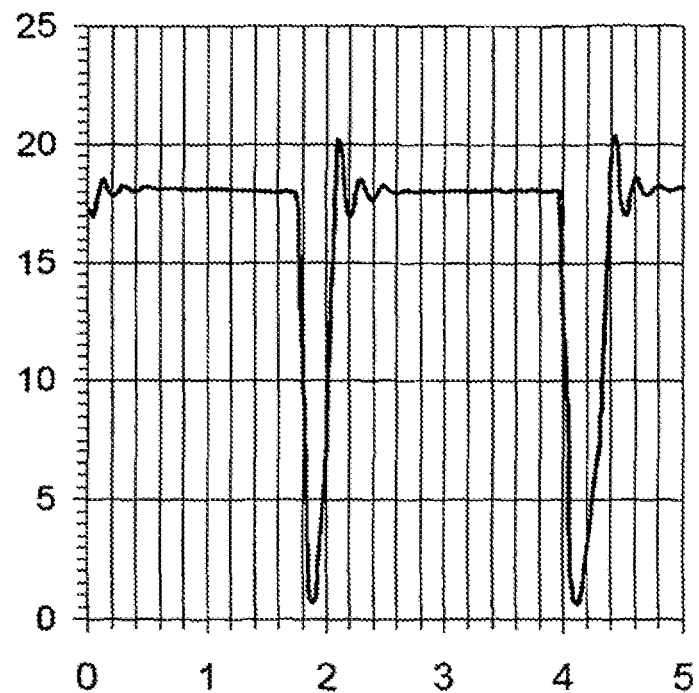
FIGS. 3A and 3B show two pressure profiles for a synchronous intensifier pump mode.
Figure 3B:
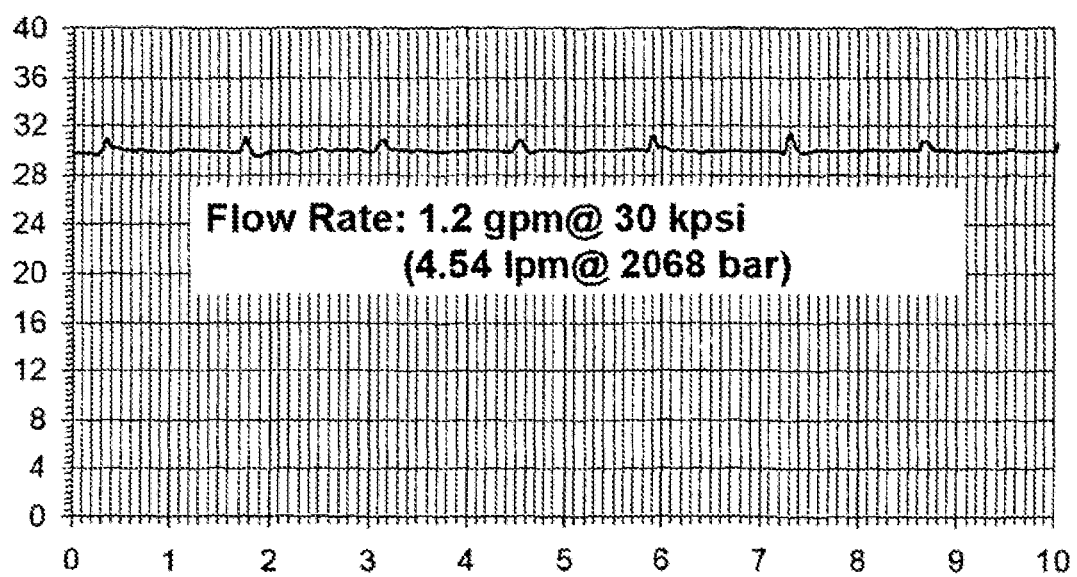

In one embodiment, the first pressure is 1300 bar±15% (18 kPSI±15%), i.e. between 1100 bar and 1500 bar (between 15 kPSI and 21 kPSI) for 85% of the time during which the emulsion is fed into the microfluidizer. Two suitable pressure profiles are shown in FIG. 3. In FIG. 3A the pressure is substantially constant for at least 85% of the time, whereas in FIG. 3B the pressure continuously remains substantially constant.

A microfluidization apparatus typically comprises at least one intensifier pump (preferably two pumps, which may be synchronous) and an interaction chamber. The intensifier pump, which is ideally electric-hydraulic driven, provides high pressure (i.e. the first pressure) to force an emulsion into and through the interaction chamber. The synchronous nature of the intensifier pumps may be used to provide the substantially constant pressure of the emulsion discussed above, which means that the emulsion droplets are all exposed to substantially the same level of shear forces during microfluidization.

One advantage of the use of a substantially constant pressure is that it can reduce fatigue failures in the microfluidization device, which may lead to longer life of the device. A further advantage of the use of a substantially constant pressure is that the parameters of the second emulsion can be improved. In particular, the number of oil droplets having a size >1.2 µm present in the second emulsion can be reduced. Furthermore, the average oil droplet size of the second emulsion can be reduced when a substantially constant pressure is used. The reduction in the average oil droplet size and in the number of oil droplets having a size >1.2 µm in the second emulsion may provide improved filtration performance. Improved filtration performance may lead to less content losses during filtration, e.g. losses of squalene, Tween 80 and Span 85 when the emulsion is MF59.

The interaction chamber may contain a plurality, e.g. 2, 3, 4, 5, 6, 7, 8, 9, 10 etc, of fixed geometry channels into which the emulsion passes. The emulsion enters the interaction chamber through an input line which may have a diameter of between 200 to 250 µm. The emulsion divides into streams as it enters the interaction chamber and, under high pressure, accelerates to high velocity. As it passes through the channels, forces produced by the high pressure may act to reduce the emulsion's oil droplet size and reduce the number of oil droplets having a size >1.2 µm. These forces can include: shear forces, through deformation of the emulsion stream occurring from contact with channel walls; impact forces, through collisions occurring when high velocity emulsion streams collide with each other; and cavitation forces, through formation and collapse of cavities within the stream. The interaction chamber usually includes no moving parts. It may include ceramic (e.g. alumina) or diamond (e.g. polycrystalline diamond) channel surfaces. Other surfaces may be made of stainless steel.

The fixed geometry of the plurality of channels in the interaction chamber may be "Y" type geometry or "Z" type geometry.

In a Y-type geometry interaction chamber a single input emulsion stream is split into first and second emulsion streams, which are then recombined into a single output emulsion stream. Prior to recombination, each of the first and second emulsion streams may independently be split into a first and second plurality (e.g. 2, 3, 4, 5, 6, 7, 8, 9, 10 etc.) of sub-streams. When the emulsion streams are recombined, the first and second emulsion streams (or their sub-streams) are ideally flowing in substantially opposite directions (e.g. the first and second emulsion streams, or their sub-streams, are flowing in substantially the same plane (±20°) and the flow direction of the first emulsion stream is 180±20° different from the flow direction of the second emulsion stream).

The forces produced when the emulsion streams are recombined may act to reduce the emulsion's oil droplet size and reduce the number of oil droplets having a size >1.2 µm.

In a Z-type geometry interaction chamber the emulsion stream passes around a plurality (e.g. 2, 3, 4, 5, 6, 7, 8, 9, 10 etc) of substantially right angled corners (i.e. 90±20°). FIG. 4 illustrates an interaction chamber with Z-type geometry and two right-angled corners in the direction of flow. During its passage around the corners, an input emulsion stream may be split into a plurality (e.g. 2, 3, 4, 5, 6, 7, 8, 9, 10 etc.) of sub-streams and then recombined into a single output emulsion stream (e.g. as shown in FIG. 4, with four sub-streams (32)). The split and then recombination (31) may occur at any point between input and output. The forces produced when the emulsion contacts the channel walls as it passes around the corners may act to reduce the emulsion's oil droplet size and reduce the number of oil droplets having a size >1.2 µm. An example of a Z-type interaction chamber is the E230Z interaction chamber from Microfluidics.

In one embodiment, the emulsion stream passes around two substantially right angled corners. At the point when the input emulsion stream passes around the first substantially right angled corner, it is split into five sub-streams. At the point when the sub-streams pass around the second substantially right angled corner, they are recombined into a single output emulsion stream.

In the prior art it has been usual to use Y-type interaction chambers for oil-in-water emulsions like those of the present invention. However, we have discovered that it is advantageous to use a Z-type channel geometry interaction chamber for oil-in-water emulsions because this can lead to a greater reduction in the number of oil droplets having a size of >1.2 µm present in the second emulsion compared to a Y-type geometry interaction chamber. The reduction in number of oil droplets having a size >1.2 µm in the second emulsion can provide improved filtration performance. Improved filtration performance may lead to less content losses during filtration, e.g. losses of squalene, Tween 80 and Span 85 when the emulsion is MF59.

A preferred microfluidization apparatus operates at a pressure between 170 bar and 2750 bar (approximately 2500 psi to 40000 psi) e.g. at about 345 bar, about 690 bar, about 1380 bar, about 2070 bar, etc.

A preferred microfluidization apparatus operates at a flow rate of up to 20 L/min e.g. up to 14 L/min, up to 7 L/min, up to 3.5 L/min, etc.

A preferred microfluidization apparatus has an interaction chamber that provides a shear rate in excess of $1 \times 10^6$ s$^{-1}$ e.g. $\geq 2.5 \times 10^6$ s$^{-1}$, $\geq 5 \times 10^6$ s$^{-1}$, $\geq 10^7$ s$^{-1}$, etc.

A microfluidization apparatus can include multiple interaction chambers that are used in parallel e.g. 2, 3, 4, 5 or more, but it is more useful to include a single interaction chamber.

The microfluidization device may comprise an auxiliary processing module (APM) comprising at least one channel. The APM contributes to the reduction in the average size of the oil droplets in the emulsion being passed through the microfluidization device, although the majority of the reduction occurs in the interaction chamber. As mentioned above, the emulsion components are introduced to the interaction chamber by the intensifier pump(s) under a first pressure. The emulsion components generally exit the APM at a second pressure which is lower than the first pressure (e.g. atmospheric pressure). In general, between 80 and 95% of the pressure difference between the first and the second pressures is dropped across the interaction chamber (e.g. from $P_1$ to $P_2$ in FIG. 4) and 5 to 20% of the pressure difference between the first and the second pressures is dropped across the auxiliary processing module, e.g. the interaction chamber may provide approximately 90% of the pressure drop while the APM may provide approximately 10% of the pressure drop. If the pressure dropped across the interaction chamber and the pressure dropped across the auxiliary processing module do not account for the whole of the pressure difference between the first and the second pressure, this can be due to a finite pressure drop across the connectors between the interaction chamber and the auxiliary processing module. The APM usually includes no moving parts. It may include ceramic (e.g. alumina) or diamond (e.g. polycrystalline diamond) channel surfaces. Other surfaces may be made of stainless steel.

The APM is generally positioned downstream of the interaction chamber and may also be positioned sequential to the interaction chamber. In the prior art, APMs are generally positioned downstream of interaction chambers comprising Y-type channels to suppress cavitation and thereby increase the flowrate in the Y-type chamber by up to 30%. Furthermore, in the prior art APMs are generally positioned upstream of interaction chambers comprising Z-type channels to reduce the size of large agglomerates. In the latter case, the APM only decreases the flowrate in the Z-type chambers by up to 3%. However, it has been found that positioning the APM downstream of an interaction chamber comprising a plurality of Z-type channels is advantageous in the present invention because it can lead to a greater reduction in average oil droplet size and a greater reduction in the number of oil droplets having a size of >1.2 µm present in the second emulsion. As discussed above, the reduction in number of oil droplets having a size >1.2 µm in the second emulsion may provide improved filtration performance. Improved filtration performance may lead to less content losses during filtration, e.g. losses of squalene, Tween 80 and Span 85 when the oil-in-water emulsion is MF59. A further advantage of this positioning of a Z-type interaction chamber and a downstream APM is that it can lead to a slower pressure decrease after the interaction chamber. The slower pressure decrease may lead to an increase in product stability because there is less gas enclosed in the emulsion.

An APM contains at least one fixed geometry channel into which the emulsion passes. The APM may contain a plurality e.g. 2, 3, 4, 5, 6, 7, 8, 9, 10 etc, of fixed geometry channels into which the emulsion passes. The channel or channels of the APM may be linear or non-linear. Suitable non-linear channels are of "Z" type geometry or "Y" type geometry, which are the same as those described above for the interaction chamber. In one embodiment, the channel, or channels, of the APM are of Z-type geometry. A plurality of Z-type channels divides the emulsion into streams as it enters the APM.

In contrast to the manufacturer's recommendations, the use of an APM comprising a plurality of fixed geometry channels is advantageous compared to a single fixed geometry channel APM because it can lead to a greater reduction in the number of oil droplets having a size >1.2 µm present in the second emulsion. As discussed above, the reduction in the number of oil droplets having a size >1.2 µm in the second emulsion can provide improved filtration performance. Improved filtration performance may lead to less content losses during filtration, e.g. losses of squalene, Tween 80 and Span 85 when the oil-in-water emulsion is MF59.

A microfluidization apparatus generates heat during operation, which can raise an emulsion's temperature by 15-20° C. relative to the first emulsion. Advantageously, therefore, the microfluidized emulsion is cooled as soon as possible. The temperature of the second emulsion may be maintained below 60° C., e.g. below 45° C. Thus an interaction chamber's output and/or an APM's output may feed into a cooling mechanism, such as a heat exchanger or cooling coil. The distance between the output and the cooling mechanism should be kept as short as possible to shorten the overall time by reducing cooling delays. In one embodiment, the distance between the output of the microfluidizer and the cooling mechanism is between 20-30 cm. A cooling mechanism is particularly useful when an emulsion is subjected to multiple microfluidization steps, to prevent over-heating of the emulsion.

The result of microfluidization is an oil-in-water emulsion, the second emulsion, in which the average size of the oil droplets is 500 nm or less. This average size is particularly useful as it facilitates filter sterilization of the emulsion. Emulsions in which at least 80% by number of the oil droplets have an average size of 500 nm or less, e.g. 400 nm or less, 300 nm of less, 200 nm or less or 165 nm or less, are particularly useful. Furthermore, the number of oil droplets in the second emulsion having a size >1.2 µm is $5\times10^{10}$/ml or less, e.g. $5\times10^9$/ml or less, $5\times10^8$/ml or less or $2\times10^8$/ml or less.

The initial input for the microfluidization may be the first emulsion. In some embodiments, however, the microfluidized emulsion is subjected to microfluidization again, such that multiple rounds of microfluidization occur. In particular, the second emulsion may be formed by circulating the second emulsion components through a microfluidization device a plurality of times, e.g. 2, 3, 4, 5, 6, 7, 8, 9, 10 etc times. The second emulsion may be formed by circulating the second emulsion components through a microfluidization device 4 to 7 times.

The circulation of the second emulsion components may comprise a type I circulation of transferring the second emulsion components between a first emulsion container (optionally having the same properties as the first premix container) and the microfluidization device.

The circulation of the second emulsion components may comprise a type II circulation of transferring the second emulsion components from a first emulsion container, through a first microfluidization device to a second emulsion container (optionally having the same properties as the first premix container), and then through a second microfluidization device.

The second microfluidization device may be the same as the first microfluidization device. Alternatively, the second microfluidization device may be different to the first microfluidization device.

The first emulsion container may be the same as the first premix container. Alternatively, the first emulsion container may be the same as the second premix container.

The second emulsion container may be the same as the first premix container. Alternatively, the second emulsion container may be the same as the second premix container.

The first emulsion container may be the same as the first premix container and the second emulsion container may be the same as the second premix container. Alternatively, the first emulsion container may be the same as the second premix container and the second emulsion container may be the same as the first premix container.

As an alternative, the first and second emulsion containers may be different to the first and second premix containers.

Following the pass of the second emulsion components through the second microfluidization device, the second emulsion components may be transferred back to the first emulsion container, for example if the type II circulation process is to be repeated. Type II circulation may be carried out a single time or a plurality of times, e.g. 2, 3, 4, 5 etc times.

Type II circulation is advantageous as it ensures that all the second emulsion components have passed through the microfluidization device at least 2 times, which reduces the average size of the oil droplets and the number of oil droplets having a size >1.2 µm in the second emulsion.

A combination of type I circulation and type II circulation may be used during microfluidization. This combination can comprise any order of type I and II circulation, e.g., type I followed by type II, type II followed by type I, type I followed by type II followed by type I again etc.

The first and second emulsion containers may be held under an inert gas, e.g. up to 0.5 bar of nitrogen. This prevents the emulsion components oxidizing, which is particularly advantageous if one of the emulsion components is squalene. This leads to an increase in the stability of the emulsion.

Methods of the invention may be used at large scale. Thus a method may involve microfluidizing a volume greater than 1 liter e.g. ≥5 liters, ≥10 liters, ≥20 liters, ≥50 liters, ≥100 liters, ≥250 liters, etc.

Filtration

After microfluidization, the second emulsion is filtered. This filtration removes any large oil droplets that have survived the homogenization and microfluidization procedures. Although small in number terms, these oil droplets can be large in volume terms and they can act as nucleation sites for aggregation, leading to emulsion degradation during storage. Moreover, this filtration step can achieve filter sterilization.

The particular filtration membrane suitable for filter sterilization depends on the fluid characteristics of the second emulsion and the degree of filtration required. A filter's characteristics can affect its suitability for filtration of the microfluidized emulsion. For example, its pore size and surface characteristics can be important, particularly when filtering a squalene-based emulsion.

The pore size of membranes used with the invention should permit passage of the desired droplets while retaining the unwanted droplets. For example, it should retain droplets that have a size of ≥1 µm while permitting passage of droplets <200 nm. A 0.2 µm or 0.22 µm filter is ideal, and can also achieve filter sterilization.

The emulsion may be prefiltered e.g. through a 0.45 µm filter. The prefiltration and filtration can be achieved in one step by the use of known double-layer filters that include a first membrane layer with larger pores and a second membrane layer with smaller pores. Double-layer filters are particularly useful with the invention. The first layer ideally has a pore size >0.3 µm, such as between 0.3-2 µm or between 0.3-1 µm, or between 0.4-0.8 µm, or between 0.5-0.7 µm. A pore size of ≤0.75 µm in the first layer is preferred. Thus the first layer may have a pore size of 0.6 µm or 0.45 µm, for example. The second layer ideally has a pore size which is less than 75% of (and ideally less than half of) the first layer's pore size, such as between 25-70% or between 25-49% of the first layer's pore size e.g. between 30-45%, such as 1/3 or 4/9, of the first layer's pore size.

Thus the second layer may have a pore size <0.3 µm, such as between 0.15-0.28 µm or between 0.18-0.24 µm e.g. a 0.2 µm or 0.22 µm pore size second layer. In one example, the first membrane layer with larger pores provides a 0.45 µm filter, while the second membrane layer with smaller pores provides a 0.22 µm filter.

The filtration membrane and/or the prefiltration membrane may be asymmetric. An asymmetric membrane is one in which the pore size varies from one side of the membrane to the other e.g. in which the pore size is larger at the entrance face than at the exit face. One side of the asymmetric membrane may be referred to as the "coarse pored surface", while the other side of the asymmetric membrane may be referred to as the "fine pored surface". In a double-layer filter, one or (ideally) both layers may be asymmetric.

The filtration membrane may be porous or homogeneous. A homogeneous membrane is usually a dense film ranging from 10 to 200 μm. A porous membrane has a porous structure. In one embodiment, the filtration membrane is porous. In a double-layer filter, both layers may be porous, both layers may be homogenous, or there may be one porous and one homogenous layer. A preferred double-layer filter is one in which both layers are porous.

In one embodiment, the second emulsion is prefiltered through an asymmetric, hydrophilic porous membrane and then filtered through another asymmetric hydrophilic porous membrane having smaller pores than the prefiltration membrane. This can use a double-layer filter.

The filter membrane(s) may be autoclaved prior to use to ensure that it is sterile.

Filtration membranes are typically made of polymeric support materials such as PTFE (poly-tetra-fluoro-ethylene), PES (polyethersulfone), PVP (polyvinyl pyrrolidone), PVDF (polyvinylidene fluoride), nylons (polyamides), PP (polypropylene), celluloses (including cellulose esters), PEEK (polyetheretherketone), nitrocellulose, etc. These have varying characteristics, with some supports being intrinsically hydrophobic (e.g. PTFE) and others being intrinsically hydrophilic (e.g. cellulose acetates). However, these intrinsic characteristics can be modified by treating the membrane surface. For instance, it is known to prepare hydrophilized or hydrophobized membranes by treating them with other materials (such as other polymers, graphite, silicone, etc.) to coat the membrane surface e.g. see section 2.1 of reference 15. In a double-layer filter the two membranes can be made of different materials or (ideally) of the same material.

An ideal filter for use with the invention has a hydrophilic surface, in contrast to the teaching of references 9-12 that hydrophobic (polysulfone) filters should be used. Filters with hydrophilic surfaces can be formed from hydrophilic materials, or by hydrophilization of hydrophobic materials, and a preferred filter for use with the invention is a hydrophilic polyethersulfone membrane. Several different methods are known to transform hydrophobic PES membranes into hydrophilic PES membranes. Often it is achieved by coating the membrane with a hydrophilic polymer. To provide permanent attachment of the hydrophilic polymer to the PES a hydrophilic coating layer is usually subjected either to a cross-linking reaction or to grafting. Reference 15 discloses a process for modifying the surface properties of a hydrophobic polymer having functionalizable chain ends, comprising contacting the polymer with a solution of a linker moiety to form a covalent link, and then contacting the reacted hydrophobic polymer with a solution of a modifying agent. Reference 16 discloses a method of PES membrane hydrophilization by direct membrane coating, involving pre-wetting with alcohol, and then soaking in an aqueous solution containing a hydrophilic monomer, a polyfunctional monomer (cross-linker) and a polymerization initiator. The monomer and cross-linker are then polymerized using thermal- or UV-initiated polymerization to form a coating of cross-linked hydrophilic polymer on the membrane surface. Similarly, references 17 and 18 disclose coating a PES membrane by soaking it in an aqueous solution of hydrophilic polymer (polyalkylene oxide) and at least one polyfunctional monomer (cross-linker), and then polymerizing a monomer to provide a non-extractable hydrophilic coating. Reference 19 describes the hydrophilization of PES membrane by a grafting reaction in which a PES membrane is submitted to low-temperature helium plasma treatment followed by grafting of hydrophilic monomer N-vinyl-2-pyrrolidone (NVP) onto the membrane surface. Further such processes are disclosed in references 20 to 26.

In methods that do not rely on coating, PES can be dissolved in a solvent, blended with a soluble hydrophilic additive, and then the blended solution is used for casting a hydrophilic membrane e.g. by precipitation or by initiating co-polymerization. Such methods are disclosed in references 27 to 33. For example, reference 33 discloses a method of preparing a hydrophilic charge-modified membrane that has low membrane extractables and allows fast recovery of ultrapure water resistivity, having a cross-linked inter-penetrating polymer network structure formed making a polymer solution of a blend of PES, PVP, polyethyleneimine, and aliphatic diglycidyl ether, forming a thin film of the solution, and precipitating the film as a membrane. A similar process is disclosed in reference 34.

Hybrid approaches can be used, in which hydrophilic additives are present during membrane formation and are also added later as a coating e.g. see reference 35.

Hydrophilization of PES membrane can also be achieved by treatment with low temperature plasmas. Reference 36 describes hydrophilic modification of PES membrane by treatment with low temperature $CO_2$-plasma.

Hydrophilization of PES membrane can also be achieved by oxidation, as described in reference 37. This method involves pre-wetting a hydrophobic PES membrane in a liquid having a low surface tension, exposing the wet PES membrane to an aqueous solution of oxidizer, and then heating.

Phase inversion can also be used, as described in reference 38.

An ideal hydrophilic PES membrane can be obtained by treatment of PES (hydrophobic) with PVP (hydrophilic). Treatment with PEG (hydrophilic) instead of PVP has been found to give a hydrophilized PES membrane that is easily fouled (particularly when using a squalene-containing emulsion) and also disadvantageously releases formaldehyde during autoclaving.

A preferred double-layer filter has a first hydrophilic PES membrane and a second hydrophilic PES membrane.

Known hydrophilic membranes include Bioassure (from Cuno); EverLUX™ polyethersulfone; STyLUX™ polyethersulfone (both from Meissner); Millex G V, Millex H P, Millipak 60, Millipak 200 and Durapore CVGLO1TP3 membranes (from Millipore); Fluorodyne™ EX EDF Membrane, Supor™ EAV; Supor™ EBV, Supor™ EKV (all from Pall); Sartopore™ (from Sartorius); Sterlitech's hydrophilic PES membrane; and Wolftechnik's WFPES PES membrane.

During filtration, the emulsion may be maintained at a temperature of 40° C. or less, e.g. 30° C. or less, to facilitate successful sterile filtration. Some emulsions may not pass through a sterile filter when they are at a temperature of greater than 40° C.

It is advantageous to carry out the filtration step within 24 hours, e.g. within 18 hours, within 12 hours, within 6 hours, within 2 hours, within 30 minutes, of producing the second emulsion because after this time it may not be possible to pass the second emulsion through the sterile filter without clogging the filter, as discussed in reference 39.

Methods of the invention may be used at large scale. Thus a method may involve filtering a volume greater than 1 liter e.g. ≥5 liters, ≥10 liters, ≥20 liters, ≥50 liters, ≥100 liters, ≥250 liters, etc.

The Final Emulsion

The result of microfluidization and filtration is an oil-in-water emulsion in which the average size of the oil droplets may be less than 220 nm, e.g. 155±20 nm, 155±10 nm or 155±5 nm, and in which the number of oil droplets having a size >1.2 μm may be $5\times10^8$/ml or less, e.g. $5\times10^7$/ml or less, $5\times10^6$/ml or less, $2\times10^6$/ml or less or $5\times10^5$/ml or less.

The average oil droplet size of emulsions described herein (including the first and second emulsions) is generally not less than 50 nm.

Methods of the invention may be used at large scale. Thus a method may involve preparing a final emulsion with a volume greater than 1 liter e.g. ≥5 liters, ≥10 liters, ≥20 liters, ≥50 liters, ≥100 liters, ≥250 liters, etc.

Once the oil-in-water emulsion has been formed, it may be transferred into sterile glass bottles. The glass bottles may be 5 L, 8 L, or 10 L in size. Alternatively, the oil-in-water may be transferred into a sterile flexible bag (flex bag). The flex bag may be 50 L, 100 L or 250 L in size. In addition, the flex bag may be fitted with one or more sterile connectors to connect the flex bag to the system. The use of a flex bag with a sterile connectors is advantageous compared to glass bottles because the flex bag is larger then the glass bottles meaning that it may not be necessary to change the flex bag to store all the emulsion manufactured in a single batch. This can provide a sterile closed system for the manufacture of the emulsion which may reduce the chance of impurities being present in the final emulsion. This can be particularly important if the final emulsion is used for pharmaceutical purposes, e.g. if the final emulsion is the MF59 adjuvant.

Preferred amounts of oil (% by volume) in the final emulsion are between 2-20% e.g. about 10%. A squalene content of about 5% or about 10% is particularly useful. A squalene content (w/v) of between 30-50 mg/ml is useful e.g. between 35-45 mg/ml, 36-42 mg/ml, 38-40 mg/ml, etc.

Preferred amounts of surfactants (% by weight) in the final emulsion are: polyoxyethylene sorbitan esters (such as Tween 80) 0.02 to 2%, in particular about 0.5% or about 1%; sorbitan esters (such as Span 85) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%. A polysorbate 80 content (w/v) of between 4-6 mg/ml is useful e.g. between 4.1-5.3 mg/ml. A sorbitan trioleate content (w/v) of between 4-6 mg/ml is useful e.g. between 4.1-5.3 mg/ml.

The process is particularly useful for preparing any of the following oil-in-water emulsions:

An emulsion comprising squalene, polysorbate 80 (Tween 80), and sorbitan trioleate (Span 85). The composition of the emulsion by volume can be about 5% squalene, about 0.5% polysorbate 80 and about 0.5% sorbitan trioleate. In weight terms, these amounts become 4.3% squalene, 0.5% polysorbate 80 and 0.48% sorbitan trioleate. This adjuvant is known as 'MF59'. The MF59 emulsion advantageously includes citrate ions e.g. 10 mM sodium citrate buffer.

Emulsions comprising squalene, an α-tocopherol (ideally DL-α-tocopherol), and polysorbate 80. These emulsions may have (by weight) from 2 to 10% squalene, from 2 to 10% α-tocopherol and from 0.3 to 3% polysorbate 80 e.g. 4.3% squalene, 4.7% α-tocopherol, 1.9% polysorbate 80. The weight ratio of squalene:tocopherol is preferably ≤1 (e.g. 0.90) as this provides a more stable emulsion. Squalene and polysorbate 80 may be present volume ratio of about 5:2, or at a weight ratio of about 11:5. One such emulsion can be made by dissolving polysorbate 80 in PBS to give a 2% solution, then mixing 90 ml of this solution with a mixture of (5 g of DL-α-tocopherol and 5 ml squalene), then microfluidizing the mixture. The resulting emulsion may have submicron oil droplets e.g. with a size between 100 and 250 nm, preferably about 180 nm.

An emulsion of squalene, a tocopherol, and a Triton detergent (e.g. Triton X-100). The emulsion may also include a 3-O-deacylated monophosphoryl lipid A ('3d-MPL'). The emulsion may contain a phosphate buffer.

An emulsion comprising squalene, a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include a 3d-MPL. The emulsion may also include a saponin, such as QS21. The aqueous phase may contain a phosphate buffer.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [40]. The emulsion may also include one or more of: alditol; a cryoprotective agent (e.g. a sugar, such as dodecylmaltoside and/or sucrose); and/or an alkylpolyglycoside. It may also include a TLR4 agonist, such as one whose chemical structure does not include a sugar ring [41]. Such emulsions may be lyophilized.

The compositions of these emulsions, expressed above in percentage terms, may be modified by dilution or concentration (e.g. by an integer, such as 2 or 3 or by a fraction, such as 2/3 or 3/4), in which their ratios stay the same. For instance, a 2-fold concentrated MF59 would have about 10% squalene, about 1% polysorbate 80 and about 1% sorbitan trioleate. Concentrated forms can be diluted (e.g. with an antigen solution) to give a desired final concentration of emulsion.

Emulsions of the invention are ideally stored at between 2° C. and 8° C. They should not be frozen. They should ideally be kept out of direct light. In particular, squalene-containing emulsions and vaccines of the invention should be protected to avoid photochemical breakdown of squalene. If emulsions of the invention are stored then this is preferably in an inert atmosphere e.g. N2 or argon.

Vaccines

Although it is possible to administer oil-in-water emulsion adjuvants on their own to patients (e.g. to provide an adjuvant effect for an antigen that has been separately administered to the patient), it is more usual to admix the adjuvant with an antigen prior to administration, to form an immunogenic composition e.g. a vaccine. Mixing of emulsion and antigen may take place extemporaneously, at the time of use, or can take place during vaccine manufacture, prior to filling. The methods of the invention can be applied in both situations.

Thus a method of the invention may include a further process step of admixing the emulsion with an antigen component. As an alternative, it may include a further step of packaging the adjuvant into a kit as a kit component together with an antigen component.

Overall, therefore, the invention can be used when preparing mixed vaccines or when preparing kits including antigen and adjuvant ready for mixing. Where mixing takes place during manufacture then the volumes of bulk antigen and emulsion that are mixed will typically be greater than 1 liter e.g. ≥5 liters, ≥10 liters, ≥20 liters, ≥50 liters, ≥100 liters, ≥250 liters, etc. Where mixing takes place at the point of use then the volumes that are mixed will typically be smaller than 1 milliliter e.g. ≤0.6 ml, ≤0.5 ml, ≤0.4 ml, ≤0.3 ml, ≤0.2 ml, etc. In both cases it is usual for substantially equal volumes of emulsion and antigen solution to be mixed i.e. substantially 1:1 (e.g. between 1.1:1 and 1:1.1, preferably between 1.05:1 and 1:1.05, and more preferably between 1.025:1 and 1:1.025). In some embodiments, however, an excess of emulsion or an excess of antigen may be used [42]. Where an excess volume of one component is used, the excess will generally be at least 1.5:1 e.g. ≥2:1, ≥2.5:1, ≥3:1, ≥4:1, ≥5:1, etc.

Where antigen and adjuvant are presented as separate components within a kit, they are physically separate from each other within the kit, and this separation can be achieved in various ways. For instance, the components may be in separate containers, such as vials. The contents of two vials can then be mixed when needed e.g. by removing the contents of one vial and adding them to the other vial, or by separately removing the contents of both vials and mixing them in a third container.

In another arrangement, one of the kit components is in a syringe and the other is in a container such as a vial. The syringe can be used (e.g. with a needle) to insert its contents into the vial for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe e.g. a dual-chamber syringe, such as those disclosed in references 43-50 etc. When the syringe is actuated (e.g. during administration to a patient) then the contents of the two chambers are mixed. This arrangement avoids the need for a separate mixing step at time of use.

The contents of the various kit components will generally all be in liquid form. In some arrangements, a component (typically the antigen component rather than the emulsion component) is in dry form (e.g. in a lyophilized form), with the other component being in liquid form. The two components can be mixed in order to reactivate the dry component and give a liquid composition for administration to a patient. A lyophilized component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses a liquid emulsion component in a pre-filled syringe and a lyophilized antigen component in a vial.

If vaccines contain components in addition to emulsion and antigen then these further components may be included in one these two kit components, or may be part of a third kit component.

Suitable containers for mixed vaccines of the invention, or for individual kit components, include vials and disposable syringes. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. In one embodiment, a vial has a butyl rubber stopper. The vial may include a single dose of vaccine/component, or it may include more than one dose (a 'multidose' vial) e.g. 10 doses. In one embodiment, a vial includes 10×0.25 ml doses of emulsion. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilized material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where a composition/component is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield.

The emulsion may be diluted with a buffer prior to packaging into a vial or a syringe. Typical buffers include: a phosphate buffer; a Tris buffer; a borate buffer; a succinate buffer; a histidine buffer; or a citrate buffer. Dilution can reduce the concentration of the adjuvant's components while retaining their relative proportions e.g. to provide a "half-strength" adjuvant.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

Various antigens can be used with oil-in-water emulsions, including but not limited to: viral antigens, such as viral surface proteins; bacterial antigens, such as protein and/or saccharide antigens; fungal antigens; parasite antigens; and tumor antigens. The invention is particularly useful for vaccines against influenza virus, HIV, hookworm, hepatitis B virus, herpes simplex virus, rabies, respiratory syncytial virus, cytomegalovirus, *Staphylococcus aureus*, chlamydia, SARS coronavirus, varicella zoster virus, *Streptococcus*

*pneumoniae, Neisseria meningitidis, Mycobacterium tuberculosis, Bacillus anthraces*, Epstein Barr virus, human papillomavirus, etc. For example:

- Influenza virus antigens. These may take the form of a live virus or an inactivated virus. Where an inactivated virus is used, the vaccine may comprise whole virion, split virion, or purified surface antigens (including hemagglutinin and, usually, also including neuraminidase). Influenza antigens can also be presented in the form of virosomes. The antigens may have any hemagglutinin subtype, selected from H1, H2, H3, H4, H5, H6, H7, H8, H9, H10, H11, H12, H13, H14, H15 and/or H16. Vaccine may include antigen(s) from one or more (e.g. 1, 2, 3, 4 or more) influenza virus strains, including influenza A virus and/or influenza B virus, e.g. a monovalent A/H5N1 or A/H1N1 vaccine, or a trivalent A/H1N1+A/H3N2+B vaccine. The influenza virus may be a reassortant strain, and may have been obtained by reverse genetics techniques [e.g. 51-55]. Thus the virus may include one or more RNA segments from a A/PR/8/34 virus (typically 6 segments from A/PR/8/34, with the HA and N segments being from a vaccine strain, i.e. a 6:2 reassortant). The viruses used as the source of the antigens can be grown either on eggs (e.g. embryonated hen eggs) or on cell culture. Where cell culture is used, the cell substrate will typically be a mammalian cell line, such as MDCK; CHO; 293T; BHK; Vero; MRC-5; PER.C6; WI-38; etc. Preferred mammalian cell lines for growing influenza viruses include: MDCK cells [56-59], derived from Madin Darby canine kidney; Vero cells [60-62], derived from African green monkey kidney; or PER.C6 cells [63], derived from human embryonic retinoblasts. Where virus has been grown on a mammalian cell line then the composition will advantageously be free from egg proteins (e.g. ovalbumin and ovomucoid) and from chicken DNA, thereby reducing allergenicity. Unit doses of vaccine are typically standardized by reference to hemagglutinin (HA) content, typically measured by SRID. Existing vaccines typically contain about 15 µg of HA per strain, although lower doses can be used, particularly when using an adjuvant. Fractional doses such as ½ (i.e. 7.5 µg HA per strain), ¼ and ⅛ have been used [64,65], as have higher doses (e.g. 3× or 9× doses [66,67]). Thus vaccines may include between 0.1 and 150 µg of HA per influenza strain, preferably between 0.1 and 50 µg e.g. 0.1-20 µg, 0.1-15 µg, 0.1-10 µg, etc. Particular doses include e.g. about 15, about 10, about 7.5, about 5, about 3.8, about 3.75, about 1.9, about 1.5, etc. per strain.
- Human immunodeficiency virus, including HIV-1 and HIV-2. The antigen will typically be an envelope antigen.
- Hepatitis B virus surface antigens. This antigen is preferably obtained by recombinant DNA methods e.g. after expression in a *Saccharomyces cerevisiae* yeast. Unlike native viral HBsAg, the recombinant yeast-expressed antigen is non-glycosylated. It can be in the form of substantially-spherical particles (average diameter of about 20 nm), including a lipid matrix comprising phospholipids. Unlike native HBsAg particles, the yeast-expressed particles may include phosphatidylinositol. The HBsAg may be from any of subtypes ayw1, ayw2, ayw3, ayw4, ayr, adw2, adw4, adrq– and adrq+.
- Hookworm, particularly as seen in canines (*Ancylostoma caninum*). This antigen may be recombinant Ac-MTP-1 (astacin-like metalloprotease) and/or an aspartic hemoglobinase (Ac-APR-1), which may be expressed in a baculovirus/insect cell system as a secreted protein [68,69].
- Herpes simplex virus antigens (HSV). A preferred HSV antigen for use with the invention is membrane glycoprotein gD. It is preferred to use gD from a HSV-2 strain ('gD2' antigen). The composition can use a form of gD in which the C-terminal membrane anchor region has been deleted [70] e.g. a truncated gD comprising amino acids 1-306 of the natural protein with the addition of aparagine and glutamine at the C-terminus. This form of the protein includes the signal peptide which is cleaved to yield a mature 283 amino acid protein. Deletion of the anchor allows the protein to be prepared in soluble form.
- Human papillomavirus antigens (HPV). Preferred HPV antigens for use with the invention are L1 capsid proteins, which can assemble to form structures known as virus-like particles (VLPs). The VLPs can be produced by recombinant expression of L1 in yeast cells (e.g. in Scerevisiae) or in insect cells (e.g. in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [71]. In addition to HPV-16 and HPV-18 strains, it is also possible to include L1 VLPs from HPV-6 and HPV-11 strains. The use of oncogenic HPV strains is also possible. A vaccine may include between 20-60 µg/ml (e.g. about 40n/ml) of L1 per HPV strain.
- Anthrax antigens. Anthrax is caused by *Bacillus anthracis*. Suitable *B. anthracis* antigens include A-components (lethal factor (LF) and edema factor (EF)), both of which can share a common B-component known as protective antigen (PA). The antigens may optionally be detoxified. Further details can be found in references [72 to 74].
- *S. aureus* antigens. A variety of *S. aureus* antigens are known. Suitable antigens include capsular saccharides (e.g. from a type 5 and/or type 8 strain) and proteins (e.g. IsdB, Hla, etc.). Capsular saccharide antigens are ideally conjugated to a carrier protein.
- *S. pneumoniae* antigens. A variety of *S. pneumoniae* antigens are known. Suitable antigens include capsular saccharides (e.g. from one or more of serotypes 1, 4, 5, 6B, 7F, 9V, 14, 18C, 19F, and/or 23F) and proteins (e.g. pneumolysin, detoxified pneumolysin, polyhistidine triad protein D (PhtD), etc.). Capsular saccharide antigens are ideally conjugated to a carrier protein.
- Cancer antigens. A variety of tumour-specific antigens are known. The invention may be used with antigens that elicit an immunotherapeutic response against lung cancer, melanoma, breast cancer, prostate cancer, etc.

A solution of the antigen will normally be mixed with the emulsion e.g. at a 1:1 volume ratio. This mixing can either be performed by a vaccine manufacturer, prior to filling, or can be performed at the point of use, by a healthcare worker.

Pharmaceutical Compositions

Compositions made using the methods of the invention are pharmaceutically acceptable. They may include components in addition to the emulsion and the optional antigen.

The composition may include a preservative such as thiomersal or 2-phenoxyethanol. It is preferred, however, that the vaccine should be substantially free from (i.e. less than 5 µg/ml) mercurial material e.g. thiomersal-free [75, 76]. Vaccines and components containing no mercury are more preferred.

The pH of a composition will generally be between 5.0 and 8.1, and more typically between 6.0 and 8.0 e.g. between 6.5 and 7.5. A process of the invention may therefore include a step of adjusting the pH of the vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunization, or may include material for multiple immunizations (i.e. a 'multidose' kit). The inclusion of a preservative is preferred in multidose arrangements.

Vaccines are typically administered in a dosage volume of about 0.5 ml, although a half dose (i.e. about 0.25 ml) may be administered to children.

Methods of Treatment, and Administration of the Vaccine

The invention provides kits and compositions prepared using the methods of the invention. The compositions prepared according to the methods of the invention are suitable for administration to human patients, and the invention provides a method of raising an immune response in a patient, comprising the step of administering such a composition to the patient.

The invention also provides these kits and compositions for use as medicaments.

The invention also provides the use of: (i) an aqueous preparation of an antigen; and (ii) an oil-in-water emulsion prepared according to the invention, in the manufacture of a medicament for raising an immune response in a patient.

The immune response raised by these methods and uses will generally include an antibody response, preferably a protective antibody response.

The compositions can be administered in various ways. The most preferred immunization route is by intramuscular injection (e.g. into the arm or leg), but other available routes include subcutaneous injection, intranasal [77-79], oral [80], intradermal [81,82], transcutaneous, transdermal [83], etc.

Vaccines prepared according to the invention may be used to treat both children and adults. The patient may be less than 1 year old, 1-5 years old, 5-15 years old, 15-55 years old, or at least 55 years old. The patient may be elderly (e.g. ≥50 years old, preferably ≥65 years), the young (e.g. ≤5 years old), hospitalized patients, healthcare workers, armed service and military personnel, pregnant women, the chronically ill, immunodeficient patients, and people travelling abroad. The vaccines are not suitable solely for these groups, however, and may be used more generally in a population.

Vaccines of the invention may be administered to patients at substantially the same time as (e.g. during the same medical consultation or visit to a healthcare professional) other vaccines.

Intermediate Processes

The invention also provides a method for the manufacture of an oil-in-water emulsion, comprising microfluidization of a first emulsion to form a second emulsion and then filtration of the second emulsion. The first emulsion has the characteristics described above.

The invention also provides a method for the manufacture of an oil-in-water emulsion, comprising filtration of a second emulsion, i.e. a microfluidized emulsion. The microfluidised emulsion has the characteristics described above.

The invention also provides a method for the manufacture of a vaccine, comprising combining an emulsion with an antigen, where the emulsion has the characteristics described above.

Specific Embodiments

Specific embodiments of the present invention include:

A method for the manufacture of a oil-in-water emulsion comprising squalene, comprising steps of (i) formation of a first emulsion having a first average oil droplet size; (ii) microfluidization of the first emulsion to form a second emulsion having a second average oil droplet size which is less than the first average oil droplet size; and (iii) filtration of the second emulsion using a hydrophilic membrane.

A method for the manufacture of a oil-in-water emulsion, comprising steps of (i) formation of a first emulsion having a first average oil droplet size of 5000 nm or less; (ii) microfluidization of the first emulsion to form a second emulsion having a second average oil droplet size which is less than the first average oil droplet size; and (iii) filtration of the second emulsion using a hydrophilic membrane.

A method for the manufacture of a oil-in-water emulsion, comprising steps of (i) formation of a first emulsion having a first average oil droplet size; (ii) microfluidization of the first emulsion to form a second emulsion having a second average oil droplet size which is less than the first average oil droplet size; and (iii) filtration of the second emulsion using a hydrophilic polyethersulfone membrane.

A method for the manufacture of an oil-in-water emulsion comprising squalene, the method comprising the step of (i) formation of a first emulsion having a first average oil droplet size using a homogenizer, wherein the first emulsion is formed by circulating the first emulsion components through a homogenizer a plurality of times.

A method for the manufacture of an oil-in-water emulsion comprising squalene, the method comprising the step of (b) microfluidization of a first emulsion having a first average oil droplet size to form a second emulsion having a second average oil droplet size which is less than the first average oil droplet size, wherein the second emulsion is formed by circulating the second emulsion components by transferring the second emulsion components from a first emulsion container, through a first microfluidization device to a second emulsion container, and then through a second microfluidization device, wherein the first and second microfluidization devices are the same.

A method for the manufacture of an oil-in-water emulsion comprising: passing a first emulsion having a first average oil droplet size through a microfluidization device to form a second emulsion having a second average oil droplet size which is less than the first average oil droplet size; wherein the microfluidization device comprises an interaction chamber which comprises a plurality of Z-type channels and an auxiliary processing module comprising at least one channel; wherein the auxiliary processing module is positioned downstream of the interaction chamber.

A method for the manufacture of an oil-in-water emulsion comprising the step of passing a first emulsion having a first average oil droplet size through a microfluidization device to form a second emulsion having a second average oil droplet size which is less than the first average oil droplet size; wherein the microfluidization device comprises an interaction chamber and an auxiliary processing module comprising a plurality of channels.

A method for the manufacture of an oil-in-water emulsion comprising the step of passing a first emulsion having a first average oil droplet size through a microfluidization device to form a second emulsion having a second average oil droplet size which is less than the first average oil droplet size, wherein the microfluidization device comprises an interaction chamber and wherein the pressure of the emulsion components at the entrance to the interaction chamber is substantially constant for at least 85% of the time during which the emulsion is fed into the microfluidizer.

A method for the manufacture of a oil-in-water emulsion, comprising the step of formation of a first emulsion having a first average oil droplet size, wherein formation of the first emulsion is carried out under an inert gas, e.g. nitrogen, e.g. at a pressure of up to 0.5 bar.

A method for the manufacture of a oil-in-water emulsion, comprising the step of passing a first emulsion having a first average oil droplet size through a microfluidization device to form a second emulsion having a second average oil droplet size which is less than the first average oil droplet size, wherein formation of the second emulsion is carried out under an inert gas, e.g. nitrogen, e.g. at a pressure of up to 0.5 bar.

A method for the manufacture of a oil-in-water emulsion, comprising steps of (i) formation of a first emulsion having a first average oil droplet size; (ii) microfluidization of the first emulsion to form a second emulsion having a second average oil droplet size which is less than the first average oil droplet size; (iii) filtration of the second emulsion; (iv) transfer of the oil-in-water emulsion into a sterile flex bag.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x+10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

MODES FOR CARRYING OUT THE INVENTION

Example 1

The emulsion components squalene, polysorbate 80, sorbitan trioleate and sodium citrate buffer were introduced into an in-line, high speed, rotor/stator homogenizer (IKA Super Dispax Reactor DRS 2000/5). Emulsion starting volumes of 280 L and 250 L were used and the speed of the homogenizer was set at 5000±1000 rpm. The temperature of the emulsion during homogenization was maintained at below 60° C.

Three test runs were carried out. In the first test run, 280 L of the emulsion components were subject to type I circulation, between the homogenizer and a first premix container, for 20 minutes followed by a single type II circulation, transferring the first emulsion components from a first premix stainless steel container, through the homogenizer to a second premix stainless steel container, and then back through the homogenizer. In the second test run, 280 L of the emulsion components were subjected to type I circulation, between the homogenizer and a first premix stainless steel container, for 5 minutes followed by 5 type II circulations, transferring the first emulsion components from a first premix stainless steel container, through the homogenizer to a second premix stainless steel container, and then back through the homogenizer to the first premix stainless steel container. In the third test run, 250 L of the emulsion components were subject to type I circulation, between the homogenizer and a first premix stainless steel container, for 20 minutes followed by a single type II circulations, transferring the first emulsion components from a first premix stainless steel container, through the homogenizer to a second premix stainless steel container, and then back through the homogenizer to the first premix stainless steel container.

The first emulsion was homogenized until it had an average oil droplet size of 1200 nm or less and a number of oil droplets having a size >1.2 μm of $5\times10^9$/ml or less.

The first emulsion was then subject to microfluidization to form a second emulsion. The emulsion was passed through the microfluidization device five times. The microfluidization device was operated at between approximately 600 and 800 bar (i.e. between approximately 9000 and 12000 psi) and the emulsion was maintained at a temperature of 40±5° C. during microfluidization through the use of a cooling mechanism.

The second emulsion was then sterile filtered.

The average size of the oil droplets in the filtered emulsions in each test run met the specification for an MF59 adjuvant.

Other parameters of the emulsions during the first, second and third test runs can be found in Table 1.

TABLE 1

| Parameter | Unit | First run | Second run | Third run |
| --- | --- | --- | --- | --- |
| Number of oil droplets with a size >1.2 μm in second emulsion | /ml | $43.7 \times 10^6$ | $56.4 \times 10^6$ | $45.1 \times 10^6$ |
| No. of oil droplets with a size >1.2 μm after filtration | /ml | $0.2 \times 10^6$ | $0.6 \times 10^6$ | $0.5 \times 10^6$ |

The results from all three test runs are excellent. However, the results in Table 1 show that test run 1 produced the largest percentage reduction (99.5%) in the number of particles with a size >1.2 μm in the emulsion after filtration compared to the number present in the second emulsion. Therefore, the best homogenization circulation pattern is about 20 minutes of type I circulation followed by a type II circulation.

Example 2

In further experiments a first emulsion was formed by type I (FIG. 5) or a type I (FIG. 5) followed by a type II (FIG. 6) circulation. For five separate runs the average number of larger particles per ml was as follows:

|  | Mean | Coefficient of variation |
| --- | --- | --- |
| Type I | $1.70 \times 10^9$ | 0.23 |
| Type I followed by Type II | $1.04 \times 10^9$ | 0.13 |

Thus the inclusion of type II circulation results in fewer large droplets and less batch-to-batch variation.

It will be understood that the invention has been described by way of example only and modifications may be made whilst remaining within the scope and spirit of the invention.

REFERENCES

[1] WO90/14837.
[2] Podda & Del Giudice (2003) *Expert Rev Vaccines* 2:197-203.
[3] Podda (2001) *Vaccine* 19: 2673-2680.
[4] *Vaccine Design: The Subunit and Adjuvant Approach* (eds. Powell & Newman) Plenum Press 1995 (ISBN 0-306-44867-X).
[5] *Vaccine Adjuvants: Preparation Methods and Research Protocols* (Volume 42 of *Methods in Molecular Medicine* series). ISBN: 1-59259-083-7. Ed. O'Hagan.
[6] *New Generation Vaccines* (eds. Levine et al.). 3rd edition, 2004. ISBN 0-8247-4071-8.
[7] O'Hagan (2007) *Expert Rev Vaccines* 6(5):699-710.
[8] EP-B-2029170
[9] Baudner et al. (2009) *Pharm Res.* 26(6):1477-85.
[10] Dupuis et al. (1999) *Vaccine* 18:434-9.
[11] Dupuis et al. (2001) *Eur J Immunol* 31:2910-8.
[12] Burke et al. (1994) *J Infect Dis* 170:1110-9.
[13] *Light Scattering from Polymer Solutions and Nanoparticle Dispersions* (W. Schartl), 2007. ISBN: 978-3-540-71950-2.
[14] Jafari et al (2008) *Food Hydrocolloids* 22:1191-1202
[15] WO90/04609.
[16] U.S. Pat. No. 4,618,533
[17] U.S. Pat. No. 6,193,077
[18] U.S. Pat. No. 6,495,050
[19] Chen et al. (1999) *Journal of Applied Polymer Science,* 72:1699-1711.
[20] U.S. Pat. No. 4,413,074
[21] U.S. Pat. No. 4,432,875
[22] U.S. Pat. No. 4,340,482
[23] U.S. Pat. No. 4,473,474
[24] U.S. Pat. No. 4,473,475
[25] U.S. Pat. No. 4,673,504
[26] EP-A-0221046.
[27] U.S. Pat. No. 4,943,374
[28] U.S. Pat. No. 6,071,406
[29] U.S. Pat. No. 4,705,753
[30] U.S. Pat. No. 5,178,765
[31] U.S. Pat. No. 6,495,043
[32] U.S. Pat. No. 6,039,872
[33] U.S. Pat. No. 5,277,812
[34] U.S. Pat. No. 5,531,893.
[35] U.S. Pat. No. 4,964,990
[36] Wavhal & Fisher (2002) *Journal of Polymer Science Part B: Polymer Physics* 40:2473-88.
[37] WO2006/044463.
[38] Espinoza-Gomez et al. (2003) *Revista de la Sociedad Quimica de Mexico* 47:53-57.
[39] Lidgate et al (1992) *Pharmaceutical Research* 9(7): 860-863.
[40] US-2007/0014805.
[41] WO2007/080308.
[42] WO2007/052155.
[43] WO2005/089837.
[44] U.S. Pat. No. 6,692,468.
[45] WO00/07647.
[46] WO99/17820.
[47] U.S. Pat. No. 5,971,953.
[48] U.S. Pat. No. 4,060,082.
[49] EP-A-0520618.
[50] WO98/01174.
[51] Hoffmann et al. (2002) *Vaccine* 20:3165-3170.
[52] Subbarao et al. (2003) *Virology* 305:192-200.
[53] Liu et al. (2003) *Virology* 314:580-590.
[54] Ozaki et al. (2004) *J. Virol.* 78:1851-1857.
[55] Webby et al. (2004) *Lancet* 363:1099-1103.
[56] WO97/37000.
[57] Brands et al. (1999) *Dev Biol Stand* 98:93-100.
[58] Halperin et al. (2002) *Vaccine* 20:1240-7.
[59] Tree et al. (2001) *Vaccine* 19:3444-50.
[60] Kistner et al. (1998) *Vaccine* 16:960-8.
[61] Kistner et al. (1999) *Dev Biol Stand* 98:101-110.
[62] Bruhl et al. (2000) *Vaccine* 19:1149-58.
[63] Pau et al. (2001) *Vaccine* 19:2716-21.
[64] WO01/22992.
[65] Hehme et al. (2004) *Virus Res.* 103(1-2):163-71.
[66] Treanor et al. (1996) *J Infect Dis* 173:1467-70.
[67] Keitel et al. (1996) *Clin Diagn Lab Immunol* 3:507-10.
[68] Williamson et al. (2006) *Infection and Immunity* 74: 961-7.
[69] Loukas et al. (2005) *PLoS Med* 2(10): e295.
[70] EP-A-0139417.
[71] Harper et al. (2004) *Lancet* 364(9447): 1757-65.
[72] *J Toxicol Clin Toxicol* (2001) 39:85-100.
[73] Demicheli et al. (1998) *Vaccine* 16:880-884.
[74] Stepanov et al. (1996) *J Biotechnol* 44:155-160.
[75] Banzhoff (2000) *Immunology Letters* 71:91-96.
[76] WO02/097072.
[77] Greenbaum et al. (2004) *Vaccine* 22:2566-77.
[78] Zurbriggen et al. (2003) *Expert Rev Vaccines* 2:295-304.
[79] Piascik (2003) *J Am Pharm Assoc* (Wash D.C.). 43:728-30.
[80] Mann et al. (2004) *Vaccine* 22:2425-9.
[81] Halperin et al. (1979) *Am J Public Health* 69:1247-50.
[82] Herbert et al. (1979) *J Infect Dis* 140:234-8.
[83] Chen et al. (2003) *Vaccine* 21:2830-6.

The invention claimed is:

1. A method for the manufacture of an emulsion, the method comprising the step of: (i) formation of a first emulsion having a first average oil droplet size by circulation, comprising (a) at least one type I circulation of transferring the first emulsion components between a first container and a homogenizer and (b) at least one type II circulation of transferring the first emulsion components from a first container to a second container through a homogenizer, and then returning them from the second container to the first container through the same homogenizer.

2. The method according to claim 1, wherein all of the emulsion components from the first container are passed through the homogenizer into the second container, and then substantially all of the emulsion components from the second container are passed through the homogenizer back into the first container.

3. The method according to claim 1, further comprising: (ii) microfluidization of the first emulsion to form a second emulsion having a second average oil droplet size which is less than the first average oil droplet size.

4. The method according to claim 1, wherein the circulation comprises (a) the at least one type I circulation followed by (b) the at least one type II circulation.

5. The method of claim 1, wherein the homogenizer is a mechanical homogenizer.

6. The method of claim 3, wherein the homogenizer provides a shear rate of up to $1\times10^6$ $s^{-1}$, and wherein the microfluidization occurs an interaction chamber that provides a shear rate $>2.5\times10^6$ $s^{-1}$.

7. The method according to claim 3, further comprising: (iii) filtration of the second emulsion.

8. The method according to claim 1, wherein step (i) comprises two or more cycles of transferring the first emulsion's components from the first container to the second container and back again.

9. The method according to claim 1, wherein during step (ii), the second emulsion is formed by circulating the second emulsion components through a microfluidization device a plurality of times.

10. The method according to claim 9, wherein the circulation of the second emulsion components comprises transferring the second emulsion components between a first emulsion container and a microfluidization device.

11. The method according to claim 9, wherein the circulation of the second emulsion components comprises transferring the second emulsion components from a first emulsion container, through a first microfluidization device to a second emulsion container, and then through a second microfluidization device, wherein the first and second microfluidization devices are the same.

12. The method according to claim 11, wherein after passing through the second microfluidization device, the second emulsion components are returned to the first emulsion container and the circulation from the first container to the second container is repeated one or more times.

13. The method according to claim 1, wherein the first average oil droplet size is 5000 nm or less.

14. The method according to claim 1, wherein the number of oil droplets having a size of $>1.2$ μm in the first emulsion is $5\times10^{11}$ /ml or less.

15. The method according to claim 3, wherein the second average oil droplet size is 500 nm or less.

16. The method according to claim 3, wherein the number of oil droplets having a size of $>1.2$ μm in the second emulsion is $5\times10^{10}$ /ml or less.

17. A method for preparing a vaccine composition, comprising preparing an emulsion according to claim 1 and combining the emulsion with an antigen.

18. A method for preparing a vaccine kit comprising preparing an emulsion according to claim 1 and packaging the emulsion into a kit as a kit component together with an antigen component.

19. The method according to claim 18, wherein the kit components are in separate vials.

20. The method according to claim 19, wherein the vials are made from borosilicate glass.

21. The method according to claim 18, wherein the emulsion is a bulk adjuvant and the method comprises extracting unit doses from the bulk adjuvant for packaging as kit components.

22. The method according to claim 17, wherein the antigen is an influenza virus antigen.

23. The method according to claim 22, wherein the combination of the emulsion and the antigen forms a vaccine composition and wherein the vaccine composition includes about 15 μg, about 10 μg, about 7.5 μg, about 5 μg, about 3.8 μg, about 1.9 μg, about 1.5 μg of hemagglutinin per influenza virus strain.

24. The method according to claim 22, wherein the combination of the emulsion and the antigen forms a vaccine composition and wherein the vaccine composition includes a thiomersal or 2-phenoxyethanol preservative.

* * * * *